US012611247B2

(12) United States Patent (10) Patent No.: US 12,611,247 B2
Tang et al. (45) Date of Patent: Apr. 28, 2026

(54) STEERABLE SHEATH AND CATHETER WITH CIRCULAR DEFLECTION

(71) Applicant: Biosense Webster (Israel) Ltd., Yokneam (IL)

(72) Inventors: Raymond Yue-Sing Tang, Rosemead, CA (US); Matthew W. Hitzeroth, Irwindale, CA (US); Daniele Ghidoli, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 785 days.

(21) Appl. No.: 17/866,740

(22) Filed: Jul. 18, 2022

(65) Prior Publication Data

US 2023/0043627 A1 Feb. 9, 2023

Related U.S. Application Data

(60) Provisional application No. 63/230,169, filed on Aug. 6, 2021.

(51) Int. Cl.
*A61B 18/14* (2006.01)
*A61B 17/00* (2006.01)
*A61B 18/00* (2006.01)

(52) U.S. Cl.
CPC .............................. *A61B 18/1492* (2013.01); *A61B 2017/00327* (2013.01); *A61B 2018/00577* (2013.01); *A61B 2018/00839* (2013.01); *A61B 2018/1435* (2013.01)

(58) Field of Classification Search
CPC ...... A61B 18/1492; A61B 2017/00327; A61B 2018/00577; A61B 2018/00839; A61B 2018/1435
See application file for complete search history.

(56) References Cited

U.S. PATENT DOCUMENTS

| | | | |
|---|---|---|---|
| 5,964,757 A | 10/1999 | Ponzi | |
| 6,224,587 B1 * | 5/2001 | Gibson | ............. A61M 25/0147 604/528 |
| 6,987,995 B2 | 1/2006 | Drysen | |
| 7,377,906 B2 | 5/2008 | Selkee | |

(Continued)

OTHER PUBLICATIONS

Extended European Search Report and Opinion dated Feb. 2, 2023, from corresponding European Application No. 22188973.6.

*Primary Examiner* — Linda C Dvorak
*Assistant Examiner* — Abigail Bock

(57) ABSTRACT

A catheter including: an elongated body sized to traverse vasculature; a lumen formed in the elongated body; and a pull-wire. The elongated body has a transition zone disposed between proximal and distal ends of the elongated body, a first shaft extending from the proximal end of the elongated body to the transition zone and defining a longitudinal axis, and a second shaft extending proximally from the distal end to the transition zone. The lumen defines a curved path curved about the longitudinal axis and extending from the distal end to the transition zone, and a straight path extending from the transition zone to the proximal end. The pull wire extends within the curved and straight paths, and is anchored to the second shaft such that translation of the pull-wire near the proximal end deflects the second shaft substantially along the curved path.

20 Claims, 18 Drawing Sheets

(56)     References Cited

U.S. PATENT DOCUMENTS

| | | | |
|---|---|---|---|
| 2014/0148759 A1* | 5/2014 | Macnamara | A61M 25/0147 |
| | | | 604/95.04 |
| 2016/0158497 A1 | 6/2016 | Tran et al. | |
| 2016/0374541 A1 | 12/2016 | Agrawal et al. | |
| 2018/0296801 A1 | 10/2018 | Tegg et al. | |
| 2019/0201688 A1 | 7/2019 | Olson | |

* cited by examiner

STEERABLE SHEATH AND CATHETER WITH CIRCULAR DEFLECTION

CROSS REFERENCE TO RELATED APPLICATION

This application claims the benefit of priority under 35 U.S.C. § 119 to prior filed U.S. Provisional Patent Application No. 63/230,169 filed on Aug. 6, 2021, which is hereby incorporated by reference as set forth in full herein.

FIELD

The present application relates generally to catheters, and specifically to steerable sheaths and catheters with circular deflection.

BACKGROUND

Deflectable or steerable catheters are used in various medical and surgical procedures, including ablation, such as arrhythmia ablation, mapping, such as cardiac mapping, and drug delivery, such as intracardial drug delivery. The steerable function can be accomplished by three modes of actions: straight translational movement along the direction of the catheter length; deflection of an end or distal section in one direction or in one plane; and turning of the catheter shaft to direct the deflected end toward the desired point. A control wire or pull wire positioned inside the catheter, usually connecting to the distal end, is used to direct the degree of deflection of the distal section. The degree of pulling on the mechanism directs the movement of the control wire and thus the degree of deflection of the distal end of the catheter shaft.

In the related art, the control wire is included within catheter is a substantially straight lumen path. Thus, deflection is generally within one plane, having only a curl or sweep profile. operably connected to some type of a pulling mechanism, which is connected to a control device at the proximal end of the catheter shaft. This type of defection creates an "S" shape between a sheath and the catheter where the deflection mechanisms are in opposing directions.

Thus, catheters capable of improved control of the distal tip and those capable of forming a loop of variable sizes are desired in the art.

SUMMARY

A catheter is presented herein which includes an elongated body sized to traverse vasculature and comprising: an outer surface, a proximal end and a distal end disposed on opposite sides thereof with a transition zone disposed therebetween, a first shaft extending distally from the proximal end of the elongated body to the transition zone and defining a longitudinal axis, a second shaft extending proximally from the distal end to the transition zone; a first lumen formed in the elongated body and defining: a first curved lumen path curved about the longitudinal axis and extending from the distal end to the transition zone, and a first straight lumen path substantially parallel to the longitudinal axis and extending from the transition zone to the proximal end; and a first pull-wire extending within the first curved and straight lumen paths, the first pull-wire being anchored to the second shaft such that translation of the first pull-wire near the proximal end deflects the second shaft substantially along the first curved lumen path.

A proximal end of the first curved lumen path can be connected to the transition zone offset approximately 90 degrees about the longitudinal axis from a distal end of the first curved lumen path connected to the distal end of the elongated body.

A proximal end of the first curved lumen path can be connected to the transition zone offset approximately 180 degrees about the longitudinal axis from a distal end of the first curved lumen path connected to the distal end of the elongated body.

The elongated body comprising a substantially circular cross section can include a diameter, a length of the second shaft being at least about two times the diameter.

The length of the second shaft can be less than about 55 millimeters.

Translation of the first pull-wire near the proximal end can deflect the second shaft substantially along the first curved lumen path forming a generally circular shape.

The catheter can further include: a second lumen formed in the elongated body, the second lumen defining a second straight lumen path substantially parallel to the longitudinal axis and extending from the distal end to the proximal end; and a second pull-wire extending within the second lumen and anchored to the distal end such that translation of the second pull-wire near the proximal end deflects the second shaft substantially along the second straight lumen path.

The catheter can further include: a second lumen formed in the elongated body, the second lumen defining a second straight lumen path substantially parallel to the longitudinal axis and extending from the proximal end to the transition zone; and a second pull-wire extending within the second lumen and anchored to the transition zone such that translation of the second pull-wire near the proximal end deflects the transition zone substantially along the second straight lumen path.

An anchor point of the second pull-wire can be located proximally along the elongated body relative to a proximal end of the first curved lumen path.

Simultaneous translation of the first pull-wire and the second pull-wire near the proximal end can deflect the second shaft substantially along the first curved lumen path and deflect the transition zone substantially along the second straight lumen path.

The catheter can further include: a second lumen formed in the elongated body and defining: a second curved lumen path curved about the longitudinal axis and extending from the distal end to the transition zone, and a second straight lumen path substantially parallel to the longitudinal axis and extending from the proximal end to the transition zone; and a second pull-wire extending within the second lumen and anchored to the second shaft such that translation of the second pull-wire near the proximal end deflects the second shaft substantially along the second curved lumen path.

The first curved lumen path may have a clockwise rotational direction about the longitudinal axis as referenced from the distal end and the second curved lumen path may have a counterclockwise rotational direction about the longitudinal axis as referenced from the distal end.

The distal end of the first curved lumen path can be offset from the distal end of the second curved lumen path.

The catheter can further include a control handle at the proximal end of the elongated body, a proximal end of the first pull-wire being attached to the control handle such that manipulating the control handle tightens the first pull-wire.

The catheter can further include a tip electrode disposed on the second shaft approximate to a distal tip of the second shaft.

The catheter can further include one or more sensing electrodes disposed on the second shaft.

The catheter can further include: a second lumen formed in the elongated body, the second lumen defining a second lumen path; a second pull-wire extending within the second lumen and anchored to the elongated body such that translation of the second pull-wire near the proximal end deflects the elongated body substantially along the second lumen path; a third lumen formed in the elongated body, the third lumen defining a third lumen path; and a third pull-wire extending within the third lumen and anchored to the elongated body such that translation of the third pull-wire near the proximal end deflects the elongated body substantially along the third lumen path.

The second lumen path can include: a second curved lumen path curved about the longitudinal axis and extending from the distal end to the transition zone, and a second straight lumen path substantially parallel to the longitudinal axis and extending from the proximal end to the transition zone. Translation of the second pull-wire near the proximal end can deflect the second shaft substantially along the second curved lumen path.

The third lumen path can be substantially parallel to the longitudinal axis and extends from the distal end to the proximal end. The third pull-wire can be anchored to the distal end such that translation of the third pull-wire near the proximal end deflects the second shaft substantially along the third lumen path.

The third lumen path can be substantially parallel to the longitudinal axis and extends from the transition zone to the proximal end. The third pull-wire can be anchored to the transition zone such that translation of the third pull-wire near the proximal end deflects the transition zone substantially along the third lumen path.

A navigable sheath is presented and includes: an elongated body having a distal end and a proximal end, the elongated body being sized to traverse vasculature and comprising: a first shaft extending distally from a proximal end of the elongated body and defining a longitudinal axis, and a second shaft extending proximally from a distal end of the elongated body, the second shaft being deflectable; a first lumen formed in the elongated body and comprising a first curved lumen path curved about the longitudinal axis and extending proximally from the distal end; and a first pull-wire extending through the first lumen and anchored to the second shaft such that translating the first pull-wire near the proximal end deflects the second shaft substantially along the first curved lumen path.

A proximal end of the first curved lumen path can be offset approximately 90 degrees about the longitudinal axis from a distal end of the first curved lumen path.

A proximal end of the first curved lumen path can be offset approximately 180 degrees about the longitudinal axis from a distal end of the first curved lumen path.

The elongated body may include a substantially circular cross section comprising a diameter, a length of the second shaft being at least about two times the diameter.

The length of the second shaft may be less than about 55 millimeters.

Translation of the first pull-wire near the proximal end may deflect the second shaft substantially along the first curved lumen path forming a generally circular shape.

The navigable sheath may further include: a second lumen formed in the elongated body, the second lumen defining a second straight lumen path substantially parallel to the longitudinal axis and extending from the distal end to the proximal end; and a second pull-wire extending within the second lumen and anchored to the distal end such that translation of the second pull-wire near the proximal end deflects the second shaft substantially along the second straight lumen path.

The navigable sheath may further include: a second lumen formed in the elongated body, the second lumen defining a second straight lumen path substantially parallel to the longitudinal axis and extending from the proximal end to the transition zone; and a second pull-wire extending within the second lumen and anchored to the transition zone such that translation of the second pull-wire near the proximal end deflects the transition zone substantially along the second straight lumen path.

An anchor point of the second pull-wire may be located proximally along the elongated body relative to a proximal end of the first curved lumen path.

Simultaneous translation of the first pull-wire and the second pull-wire near the proximal end may deflect the second shaft substantially along the first curved lumen path and deflects the transition zone substantially along the second straight lumen path.

The navigable sheath may further include: a second lumen formed in the elongated body and defining: a second curved lumen path curved about the longitudinal axis and extending from the distal end to the transition zone, and a second straight lumen path substantially parallel to the longitudinal axis and extending from the proximal end to the transition zone; and a second pull-wire extending within the second lumen and anchored to the second shaft such that translation of the second pull-wire near the proximal end deflects the second shaft substantially along the second curved lumen path.

The first curved lumen path may have a clockwise rotational direction about the longitudinal axis as referenced from the distal end and the second curved lumen path may have a counterclockwise rotational direction about the longitudinal axis as referenced from the distal end.

The distal end of the first curved lumen path may be offset from the distal end of the second curved lumen path.

The navigable sheath may further include: a second lumen formed in the elongated body, the second lumen defining a second lumen path; a second pull-wire extending within the second lumen and anchored to the elongated body such that translation of the second pull-wire near the proximal end deflects the elongated body substantially along the second lumen path; a third lumen formed in the elongated body, the third lumen defining a third lumen path; and a third pull-wire extending within the third lumen and anchored to the elongated body such that translation of the third pull-wire near the proximal end deflects the elongated body substantially along the third lumen path.

The second lumen path may include: a second curved lumen path curved about the longitudinal axis and extending from the distal end to the transition zone, and a second straight lumen path substantially parallel to the longitudinal axis and extending from the proximal end to the transition zone. Translation of the second pull-wire near the proximal end may deflect the second shaft substantially along the second curved lumen path.

The third lumen path may be substantially parallel to the longitudinal axis and extends from the distal end to the proximal end. The third pull-wire may be anchored to the distal end such that translation of the third pull-wire near the proximal end deflects the second shaft substantially along the third lumen path.

The third lumen path may be substantially parallel to the longitudinal axis and extends from the transition zone to the proximal end. the third pull-wire may be anchored to the transition zone such that translation of the third pull-wire near the proximal end deflects the transition zone substantially along the third lumen path.

A method of using a using a catheter in a patient is presented, the method including: inserting into the patient a distal end of an elongated body of the catheter, the catheter comprising: a first shaft extending distally from a proximal end of the elongated body, a second shaft extending proximally from the distal end and defining a longitudinal axis, a first pull-wire disposed within the elongated body along a curved path curved about the longitudinal axis and extending from the distal end, and a second pull-wire disposed within the elongated body along a straight path substantially parallel to the longitudinal axis; pulling the first pull-wire to deflect the second shaft substantially along the curved path; and pulling the second pull-wire to deflect the second shaft substantially along the straight path.

The method may further include: sensing electrical activity from one or more sensors disposed along the second shaft while the second shaft is deflected substantially along the curved path; maneuvering a distal tip of the distal end to contact tissue of the patient; and energizing a tip electrode disposed on the second shaft approximate to the distal tip to ablate the tissue of the patient.

A proximal end of the first curved path may be connected to the transition zone offset approximately 90 degrees about the longitudinal axis from a distal end of the first curved path connected to the distal end of the elongated body.

A proximal end of the first curved path may be connected to the transition zone offset approximately 180 degrees about the longitudinal axis from a distal end of the first curved path connected to the distal end of the elongated body.

The elongated body may include a substantially circular cross section comprising a diameter, a length of the second shaft being at least about two times the diameter.

The length of the second shaft may be less than about 55 millimeters.

The method may include pulling of the first pull-wire deflecting the second shaft substantially along the first curved path forming a generally circular shape.

The second pull-wire may be anchored to the distal end.

The second pull-wire may be anchored to the transition zone.

An anchor point of the second pull-wire may be located proximally along the elongated body relative to a proximal end of the first curved path.

The method may include contemporaneously pulling of the first pull-wire and the second pull-wire to deflect the second shaft substantially along the first curved path and deflect the transition zone substantially along the first straight path.

The catheter may further include a third pull-wire disposed within the elongated body along a second curved path curved about the longitudinal axis and extending from the distal end. The method may further include pulling the third pull-wire to deflect the second shaft substantially along the second curved path.

The first curved path may have a clockwise rotational direction about the longitudinal axis as referenced from the distal end and the second curved lumen path may have a counterclockwise rotational direction about the longitudinal axis as referenced from the distal end.

The distal end of the first curved path may be offset from the distal end of the second curved lumen path.

The method may further including manipulating a control handle at the proximal end of the elongated body, to pull the first pull-wire and the second pull-wire.

The catheter may further include a third pull-wire disposed within the elongated body along a second straight path substantially parallel to the longitudinal axis and extending from the proximal end. The method may further include pulling the third pull-wire to deflect the second shaft substantially along the second straight path.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

Figure 1A:
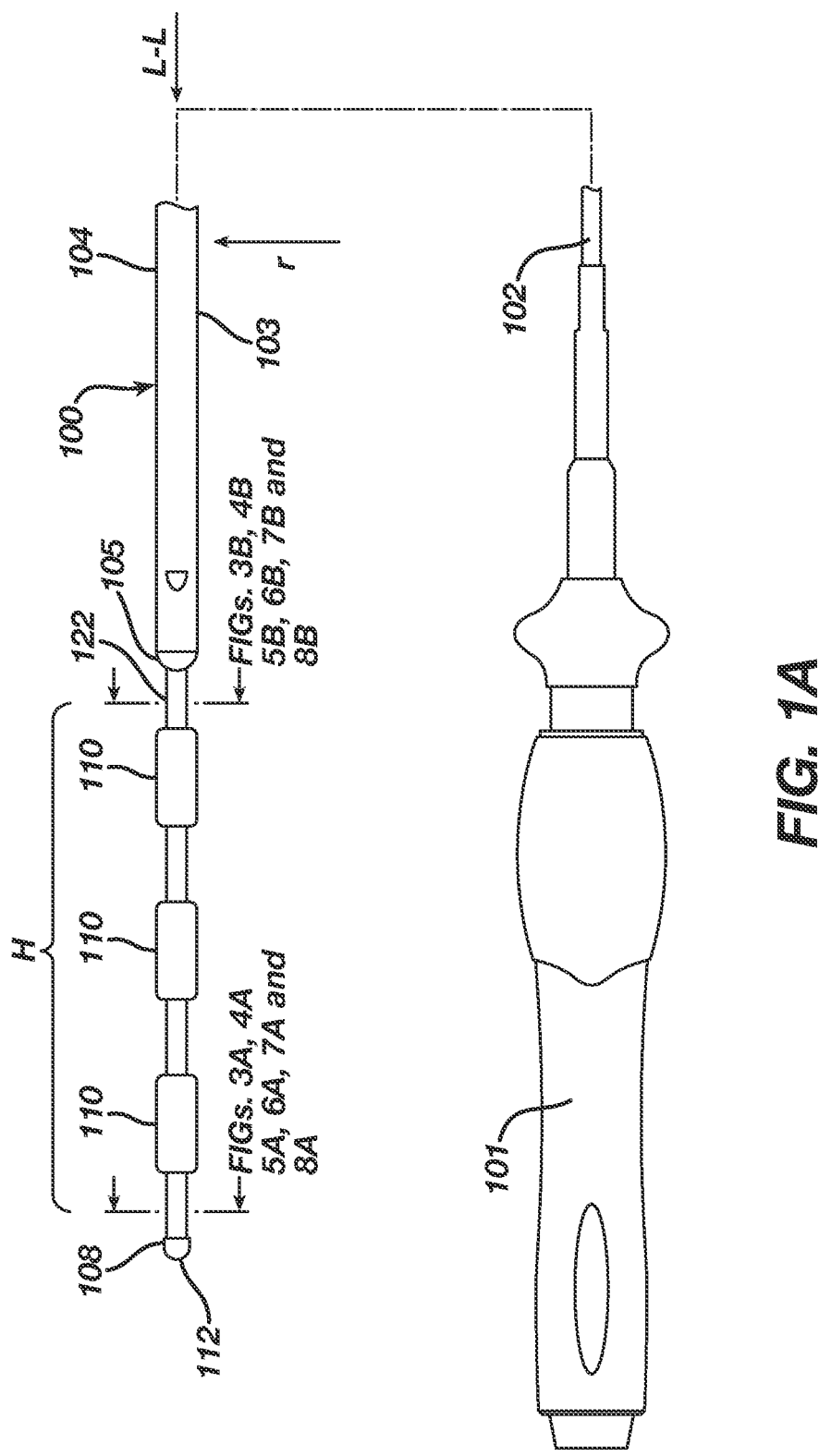
FIG. 1A illustrates an example catheter in a delivery configuration according to aspects of the present invention.
Figure 1B:
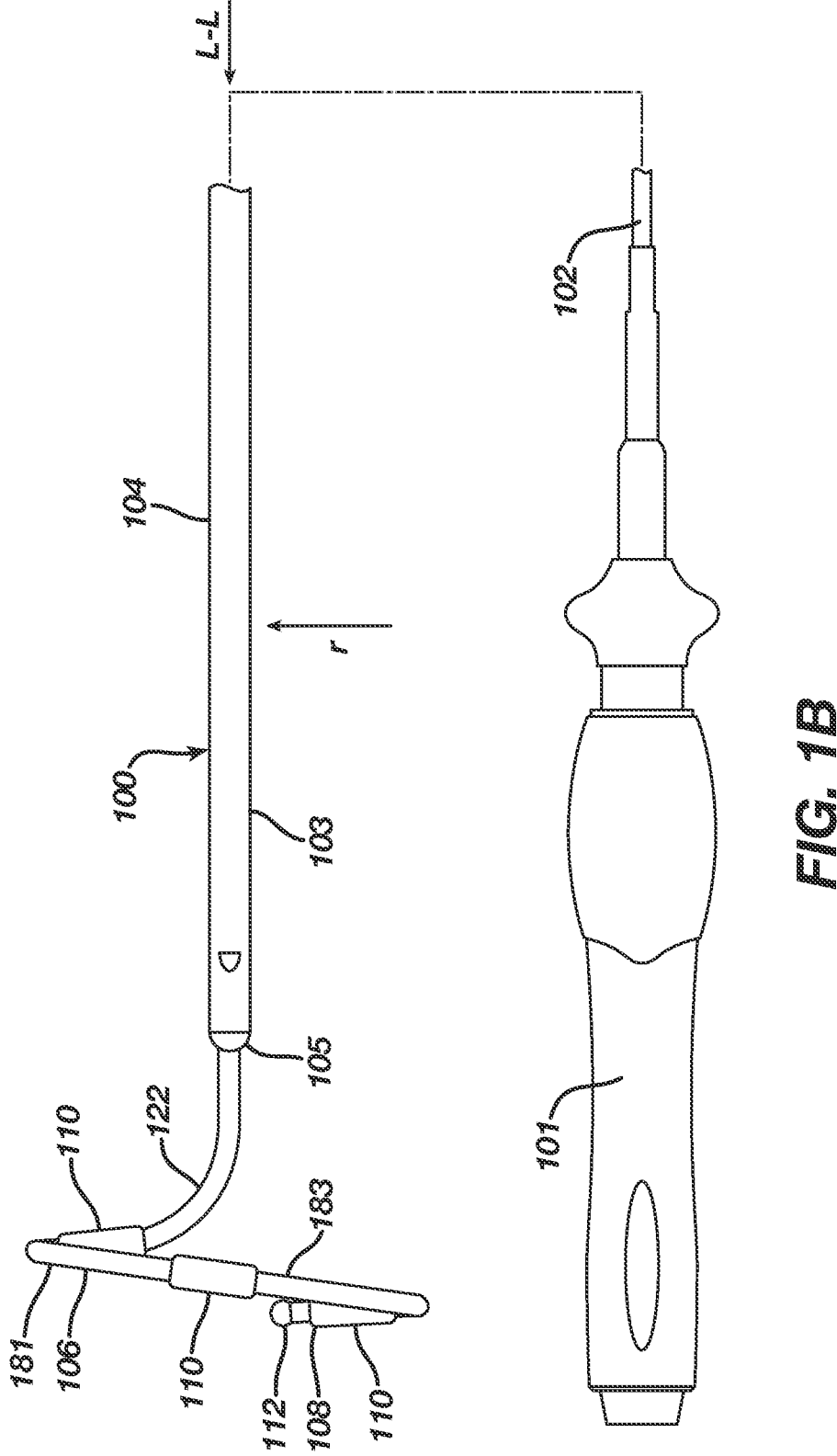
FIG. 1B illustrates the catheter in a deployed configuration according to aspects of the present disclosure.

FIGS. 1A and 1B illustrate an example catheter 100 which includes inductive sensors 110 including inductive coils which conform to the curved surface of a tubular catheter body 103 (specifically to a cylindrical surface 183 of a distal shaft 106 of the tubular body 103) and collectively can function as a three axis sensor during an intravascular treatment. The inductive sensors 110 can be fabricated on a flexible circuit 181 and affixed to the tubular catheter body 103. The sensors 110 can include mapping electrodes 110 and can be positioned and otherwise configured to measure electrical signals from tissue in contact with the distal shaft 106.

FIG. 1A illustrates the tubular body 103 of the catheter 100 in a delivery configuration in which the distal shaft 106 and proximal shaft 104 are aligned along a longitudinal axis L-L with an oriented radial direction r. A length of the distal shaft 106 is H, and a diameter of the catheter is D1. The cylindrical surface 183 of the distal shaft 106 curves around the longitudinal axis when the tubular body 103 is in the delivery configuration. The circuit 181 can be affixed to the cylindrical surface 183 such that the inductive sensors 110 each conform to the curvature of the cylindrical surface. An ablation electrode 112 can be disposed on the distal end 108.

As illustrated in FIG. 1B, the distal shaft 106 of the tubular body 103 can be moved into a generally circular shape when within the vasculature or a heart. The generally circular shape can be slightly helical ("lasso"). The circular shape can curve in the clockwise or counterclockwise direction. The inductive sensors 110 can be positioned around the circular shape such that a position and orientation of the distal shaft 106 can be determined in three dimensions when the distal shaft 106 is within a known varying magnetic field.

The catheter 100 can include a control handle 101 affixed to a proximal end 102 of the tubular body 103 that can be moved to push the tubular body 103 distally through vasculature. In some examples, the control handle 101 can also be used to move the distal shaft 106 from the delivery configuration illustrated in FIG. 1A to the deployed configuration illustrated in FIG. 1B and vice versa similar to a multifunctional catheter handle and corresponding catheter as disclosed in U.S. Pat. No. 6,987,995 which is hereby incorporated by reference in its entirety into this application as if set forth in full, or an alternative system capable of causing the distal shaft 106 to move to an expanded deployed shape.

As illustrated in FIGS. 1A and 1B, the tubular body 103 can have a deployed configuration in which the distal shaft 106 has a generally circular shape. The circular shape can have a diameter of D2 (see, e.g., FIGS. 11 and 12). The circular shape can be generally orthogonal to the longitudinal axis L-L defined by the proximal shaft 104 of the tubular body. Alternatively, the circular shape can be aligned to the longitudinal axis L-L or at an oblique angle to the longitudinal axis L-L. As illustrated, the distal shaft 106 forms a lasso shape that is generally orthogonal to the longitudinal axis L-L of the shaft 104. Regardless of the angle of the circular shape to the longitudinal axis L-L, when the distal shaft 106 is in the generally circular shape, the inductive sensors 110 can be spaced approximately equidistant from each other around the generally circular shape.

The proximal shaft 104 can have an elongated tubular construction. The proximal shaft 104 can have a single, axial, or central lumen. The proximal shaft 104 can be flexible, i.e., bendable, but substantially non-compressible along its length. The proximal shaft 104 can be of any suitable construction and made of any suitable material. In some examples, the proximal shaft 104 has an outer polymer wall having an interior braided metal mesh. The proximal shaft 104 can have sufficient structural integrity such that when the control handle 101 is rotated, the tubular body 103, including the proximal shaft 104 and distal shaft 106, rotate in a corresponding manner. The outer diameter of the proximal shaft 104 is preferably about 8 French or about 7 French.

The useful length of the catheter 100, i.e., that portion that can be inserted into the body, can vary as appropriate based on treatment procedure and anatomy of a patient. For most treatments, the useful length can be about 181 centimeters (cm) to about 120 cm. The length of the distal shaft 106 is a relatively small portion of the useful length and preferably is about 3.5 cm to about 10 cm, and more preferably about 5 cm to about 6.5 cm.

In some examples, the distal shaft 106 can have a section aligned with the longitudinal axis L-L, when the distal shaft 106 is in the substantially circular shape, measuring about 3 millimeters (mm) to about 12 mm. The distal end 108 of the tubular body 103 may or may not overlap the distal shaft 106 when in the circular shape (e.g. comparing FIG. 1B with FIGS. 11). The generally circular shape can have a circumference measuring approximately equal to the length of the distal shaft 106 or may deviate from the length of the distal shaft 106 somewhat. Further, in some examples, the circumference of the circular shape can be modified in patient via manipulation of the control handle 101. The circular shape can have a circumference measuring about 3 cm to about 8 cm, more preferably about 4 cm to about 6 cm, and more preferably about 5 cm.

The proximal shaft 104 and distal shaft 106 can be joined with glue or the like through a transition zone/region/point 122. In some examples, the junction 105 can include a spacer similar to the one as described in U.S. Pat. No. 5,964,757 which is hereby incorporated by reference in its entirety into this application as if set forth in full.

Figure 2B:
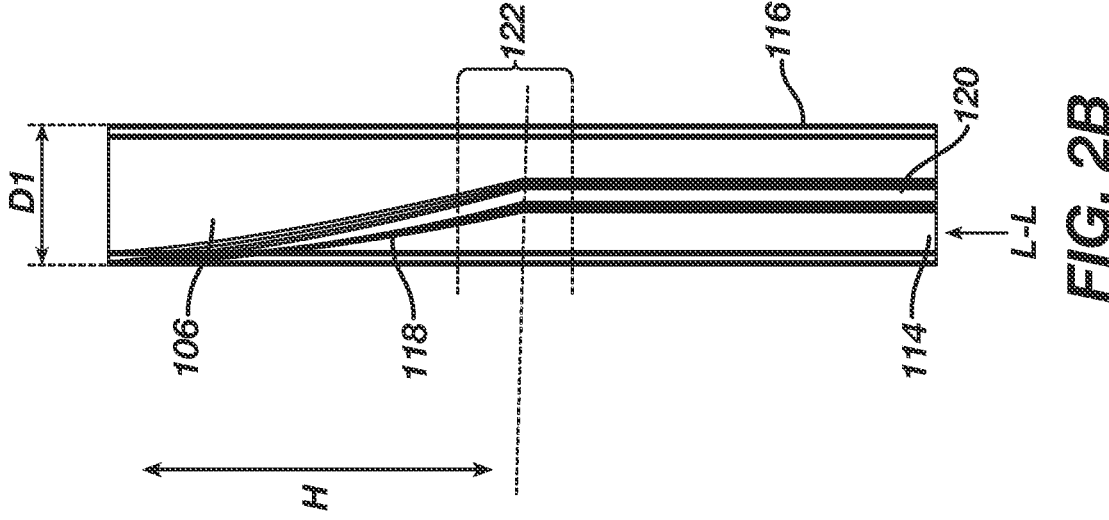
FIGS. 2A-2F illustrate various examples of lumens of the catheter as indicated in FIGS. 1A & 1B according to aspects of the present disclosure.
Figure 2A:
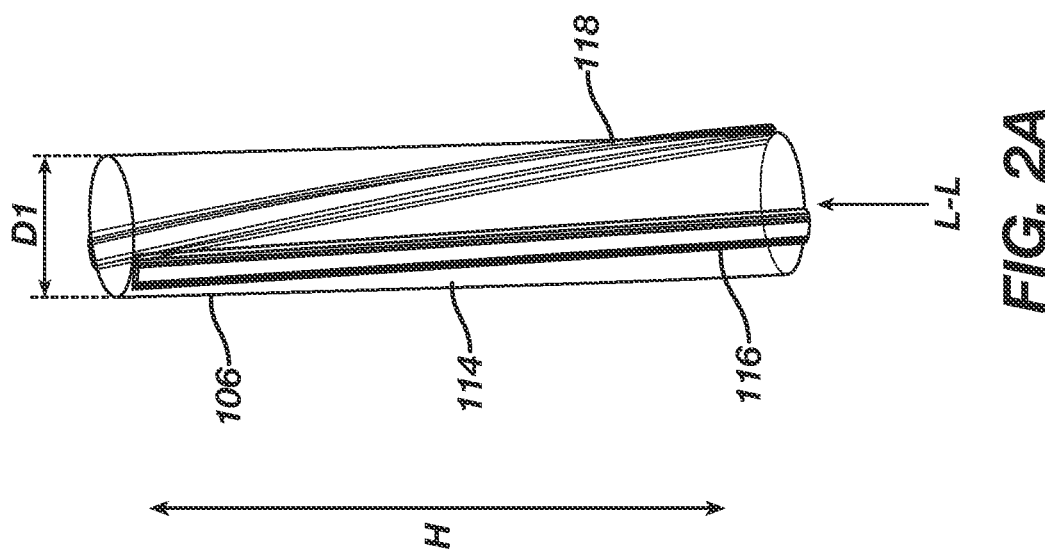

FIGS. 2A-2F illustrate example see through views of a catheter tube 114. In FIG. 2A, a substantially straight lumen 116 and a curved lumen 118 are formed and/or disposed on or near a surface of the sheath 114 having a diameter D1. The straight lumen 116 defines a substantially straight path and the curved lumen 118 defines curved path curved about the longitudinal axis L-L. Pull wires 126 (see, FIGS. 12A-14B) can be disposed in the lumens 116 and 118 and attached to the distal end 108. When the pull wire 126 in the straight lumen 116 is translated (e.g., pulled from the proximal end 102 or modulated using control handle 101), the distal shaft 106 deflects along the straight path, for example, in a curl or sweep profile. When the pull wire 126 in the curved lumen 118 is translated (e.g., pulled from the proximal end 102 or modulated using control handle 101), the distal shaft 106 deflects along the curved path, for example, forming a lasso or loop. It may not be possible to translate the pull wires 126 in both the straight lumen 116 and curved lumen 118 simultaneously.

In FIG. 2B, a substantially straight lumen 116 and a curved lumen 118 are formed and/or disposed on or near a surface of the sheath 114 having a diameter D1. The straight lumen 116 defines a substantially straight path from the distal end 108 through the transition zone 122 and to the proximal shaft 104. The curved lumen 118 defines curved path curved about the longitudinal axis L-L over the distal shaft 106. The curved lumen 118 attaches to a straight, shortened lumen 120 at the transition zone 122. Thus, the curved lumen 118 may only be curved about the distal shaft 106 (e.g., where the catheter 100 deflects) and substantially straight about the proximal shaft 104. Pull wires 126 (see, FIGS. 12A-14B) can be disposed in the lumens 116 and 118 and attached to the distal end 108. When the pull wire 126 in the straight lumen 116 is translated (e.g., pulled from the proximal end 102 or modulated using control handle 101), the distal shaft 106 deflects along the straight path, for example, in a curl or sweep profile. When the pull wire 126 in the curved lumen 118 is translated (e.g., pulled from the proximal end 102 or modulated using control handle 101), the distal shaft 106 deflects along the curved path, for example, forming a lasso or loop. It may not be possible to translate the pull wires 126 in both the straight lumen 116 and curved lumen 118 simultaneously.

An additional pull wire 126 may be disposed in the shortened lumen 120 that attaches to the transition zone 122. When the pull wire 126 in the shortened lumen 120 is translated (e.g., pulled from the proximal end 102 or modulated using control handle 101), the catheter 100 deflects about the transition zone 122 along the shortened path, for example, bending the catheter 100 at the transition zone 122. It may be possible to translate the pull wire 126 in the shortened lumen 120 at the same time as translating the pull wires 126 either the straight lumen 116 or the curved lumen 118 in order to change an orientation of the shape of the catheter 100 formed by the straight lumen 116 or the curved lumen 118. In some cases, multiple pull wires 126 may be included in a single lumen. For example, a first pull wire 126 may be attached to catheter 100 at or near the transition zone such that translating the pull wire 126 deflects the catheter 100 about the transition zone 122 along a shortened path (e.g., similar to pull wire 126 in the shortened lumen 120), while a second pull wire 126 may be attached to catheter 100 at or near a distal end of the lumen (e.g., similar to pull wire 126 in straight lumen 116 or pull wire 126 in curved lumen 118).

Figure 2D:
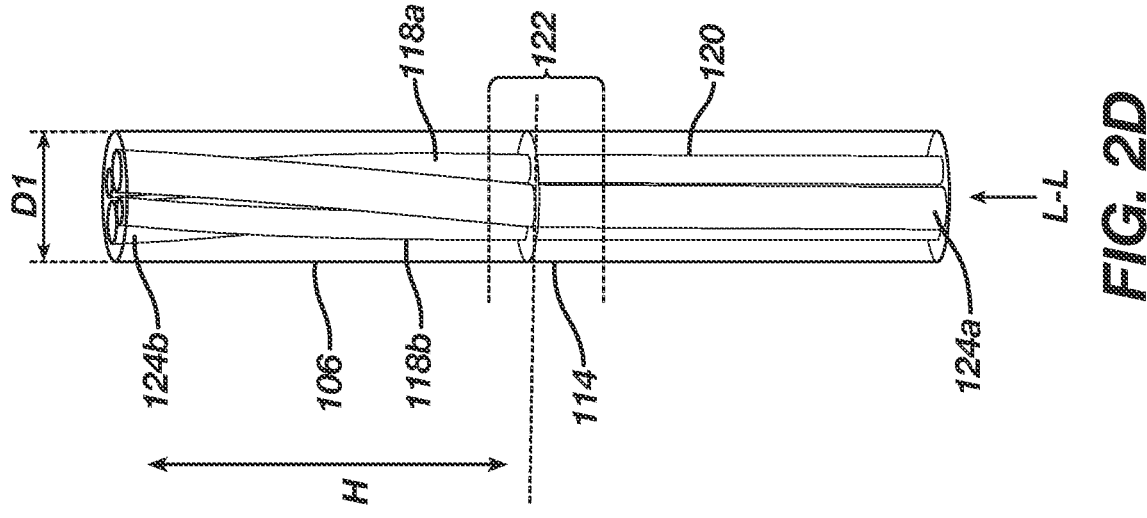
Figure 2C:
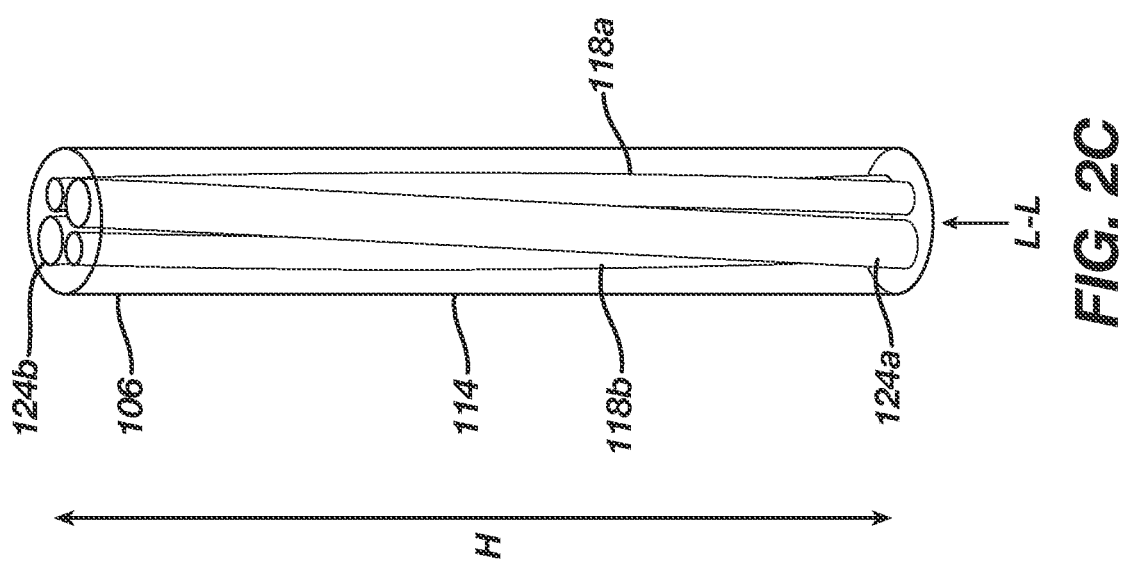

In FIG. 2C, two curved lumens 118a and 118b are formed within catheter sheath 114. The curved lumens 118a and 118b define curved paths curved about the longitudinal axis L-L. Function lumens 124a and 124b are also formed in catheter sheath 114. The function lumens 124a and 124b allow for sensors, power, and/or tools to pass through the catheter 100. Pull wires 126 (see, FIGS. 12A-14B) can be disposed in the curved lumens 118a and 118b and attached to the distal end 108. When the pull wire 126 in either curved lumen 118a and 118b is translated (e.g., pulled from the proximal end 102 or modulated using control handle 101), the distal shaft 106 deflects along the respective curved path, for example, forming a lasso or loop. It may not be possible to translate the pull wires 126 in both the curved lumen 118a and 118b simultaneously. Rather, translating the pull wires 126 individually can create loops of different sizes and/or orientations.

In FIG. 2D, two curved lumens 118a and 118b are formed within catheter sheath 114. The curved lumens 118a and 118b define curved paths curved about the longitudinal axis L-L. Function lumens 124a and 124b are also formed in catheter sheath 114. The function lumens 124a and 124b allow for sensors, power, and/or tools to pass through the catheter 100. The first curved lumen 118a attaches to a straight, shortened lumen 120 at the transition zone 122. Thus, the first curved lumen 118a may only be curved about the distal shaft 106 (e.g., where the catheter 100 deflects) and substantially straight about the proximal shaft 104. Pull wires 126 (see, FIGS. 12A-14B) can be disposed in the curved lumens 118a and 118b and attached to the distal end 108. When the pull wire 126 in either curved lumen 118a and 118b is translated (e.g., pulled from the proximal end 102 or modulated using control handle 101), the distal shaft 106 deflects along the respective curved path, for example, forming a lasso or loop. It may not be possible to translate the pull wires 126 in both the curved lumen 118a and 118b simultaneously. Rather, translating the pull wires 126 individually can create loops of different sizes and/or orientations. An additional pull wire 126 may be disposed in the shortened lumen 120 that attaches to the transition zone 122. When the pull wire 126 in the shortened lumen 120 is translated (e.g., pulled from the proximal end 102 or modulated using control handle 101), the catheter 100 deflects about the transition zone 122 along the shortened path, for example, bending the catheter 100 at the transition zone 122. It may be possible to translate the pull wire 126 in the shortened lumen 120 at the same time as translating either pull wires 126 in the curved lumens 118a and 118b in order to change an orientation of the shape of the catheter 100 formed by the curved lumens 118a and 118b.

Figure 2F:
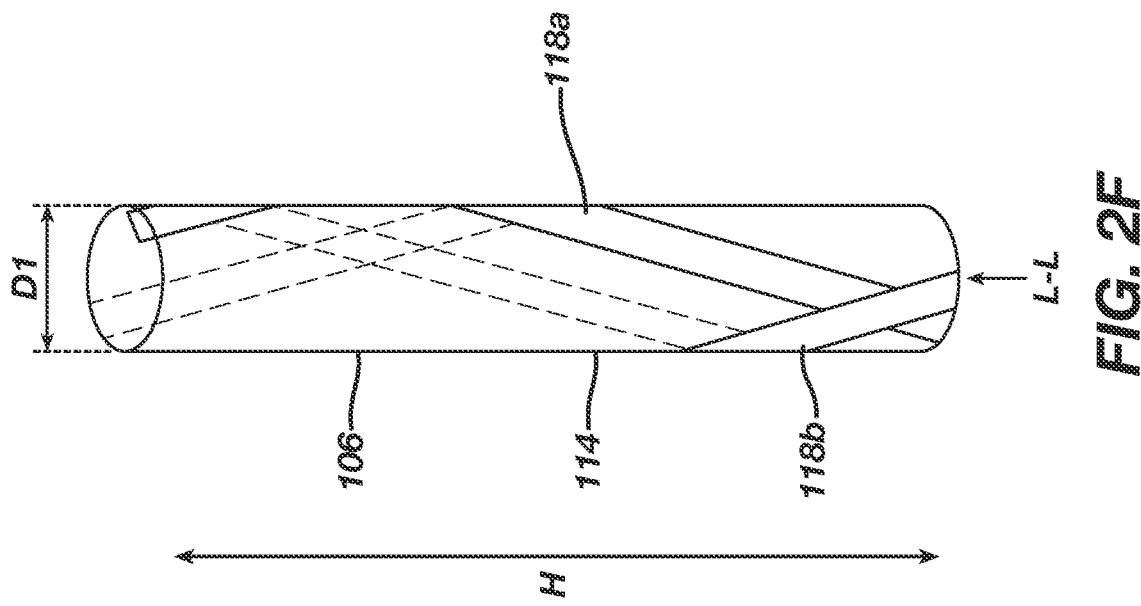
Figure 2E:
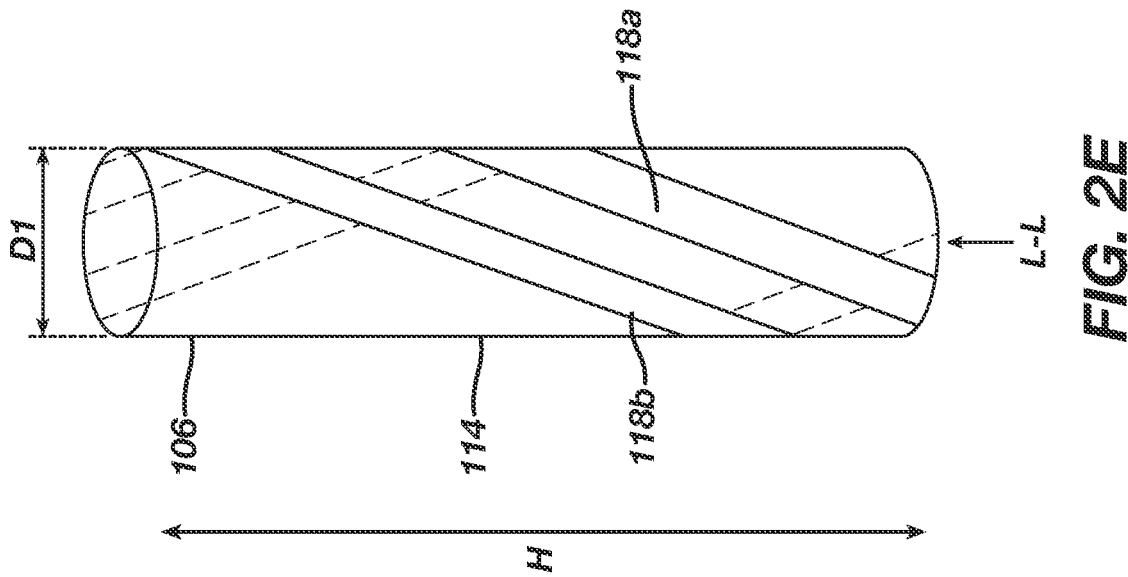

In FIG. 2E, two curved lumens 118a and 118b are formed and/or disposed on or near a surface of the sheath 114 having a diameter D1. The curved lumens 118a and 118b define curved paths curved about the longitudinal axis L-L. The curved paths defined by the curved lumens 118a and 118b may have different lengths and/or pitches. Pull wires 126 (see, FIGS. 12A-14B) can be disposed in the curved lumens 118a and 118b and attached to the distal end 108. When the pull wire 126 in either curved lumen 118a and 118b is translated (e.g., pulled from the proximal end 102 or modulated using control handle 101), the distal shaft 106 deflects along the respective curved path, for example, forming a lasso or loop. It may not be possible to translate the pull wires 126 in both the curved lumen 118a and 118b simultaneously. Rather, translating the pull wires 126 individually can create loops of different sizes and/or orientations.

In FIG. 2F, two curved lumens 118a and 118b are formed and/or disposed on or near a surface of the sheath 114 having a diameter D1. The curved lumens 118a and 118b define curved paths curved about the longitudinal axis L-L. The curved paths defined by the curved lumens 118a and 118b may have rotational directions (e.g., "handedness"), lengths and/or pitches. Pull wires 126 (see, FIGS. 12A-14B) can be disposed in the curved lumens 118a and 118b and attached to the distal end 108. When the pull wire 126 in either curved lumen 118a and 118b is translated (e.g., pulled from the proximal end 102 or modulated using control handle 101), the distal shaft 106 deflects along the respective curved path, for example, forming a lasso or loop. It may not be possible to translate the pull wires 126 in both the curved lumen 118a and 118b simultaneously. Rather, translating the pull wires 126 individually can create loops of different sizes and/or orientations.

Figure 3B:
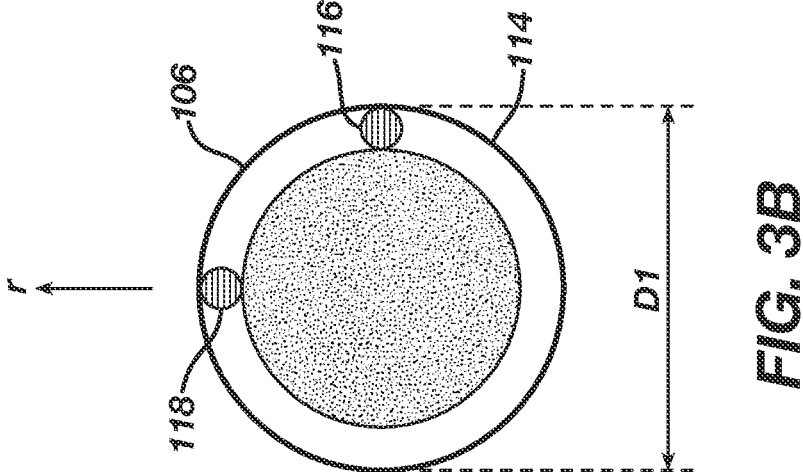
FIGS. 3A-10B illustrate example cross-sections of the catheter as indicated in FIGS. 1A & 1B according to aspects of the present disclosure.
Figure 3A:
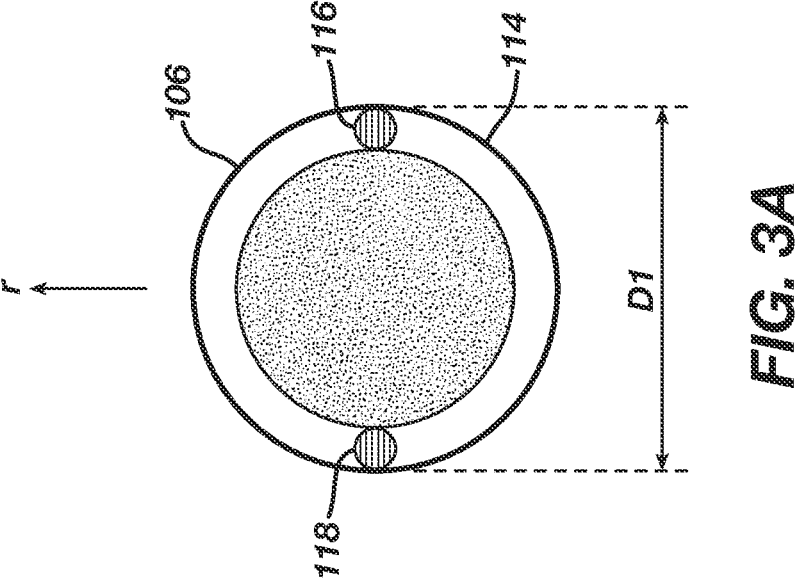

FIGS. 3A and 3B illustrate two example cross-sections of the catheter as indicated in FIGS. 1A & 1B according to aspects of the present disclosure. In particular, FIG. 3A is a cross-sectional view of the distal shaft 106 near the distal end 108 and FIG. 3B is a cross-sectional view of the distal shaft 106 near the transition zone 122. As can be seen, the catheter 100 includes a straight lumen 116 and a curved lumen 118. The curved lumen rotates 90 degrees around the catheter body 103 as it moves from the distal end 108 to the transition zone 122. Thus, when the pull wire 126 in the curved lumen 118 is translated (e.g., pulled from the proximal end 102 or modulated using control handle 101), the distal shaft 106 deflects along the curved path, for example, forming a lasso or loop.

Figure 4B:
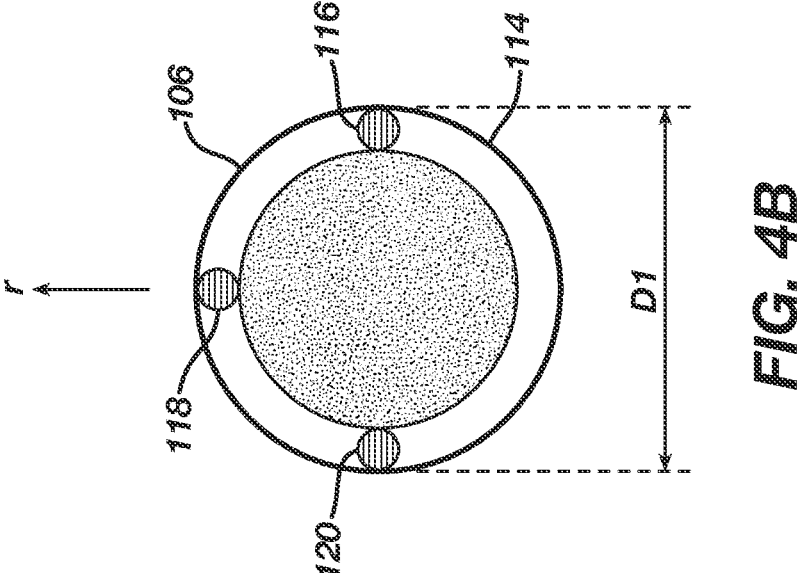
Figure 4A:
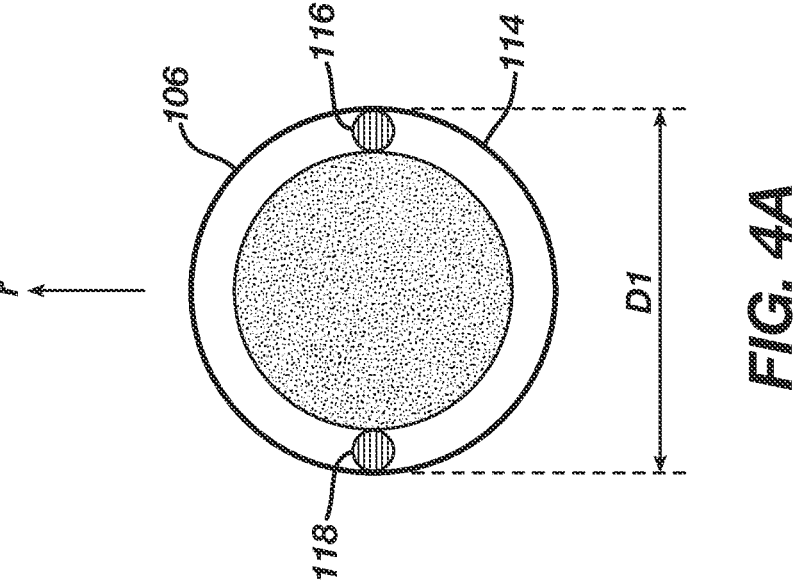

FIGS. 4A and 4B illustrate two example cross-sections of the catheter as indicated in FIGS. 1A & 1B according to aspects of the present disclosure. In particular, FIG. 4A is a cross-sectional view of the distal shaft 106 near the distal end 108 and FIG. 4B is a cross-sectional view of the distal shaft 106 near the transition zone 122. As can be seen, the catheter 100 includes a straight lumen 116, a curved lumen 118, and a shortened lumen 120. The curved lumen rotates 90 degrees around the catheter body 103 as it moves from the distal end 108 to the transition zone 122. Thus, when the pull wire 126 in the curved lumen 118 is translated (e.g., pulled from the proximal end 102 or modulated using control handle 101), the distal shaft 106 deflects along the curved path, for example, forming a lasso or loop. The shortened lumen 120 stops between the transition zone 122 and the distal end 108. When the pull wire 126 in the shortened lumen 120 is translated (e.g., pulled from the proximal end 102 or modulated using control handle 101), the catheter 100 deflects about the transition zone 122 along the shortened path, for example, bending the catheter 100 at the transition zone 122. It may be possible to translate the pull wire 126 in the shortened lumen 120 at the same time as translating the pull wires 126 either the straight lumen 116 or the curved lumen 118 in order to change an orientation of the shape of the catheter 100 formed by the straight lumen 116 or the curved lumen 118.

Figure 5B:
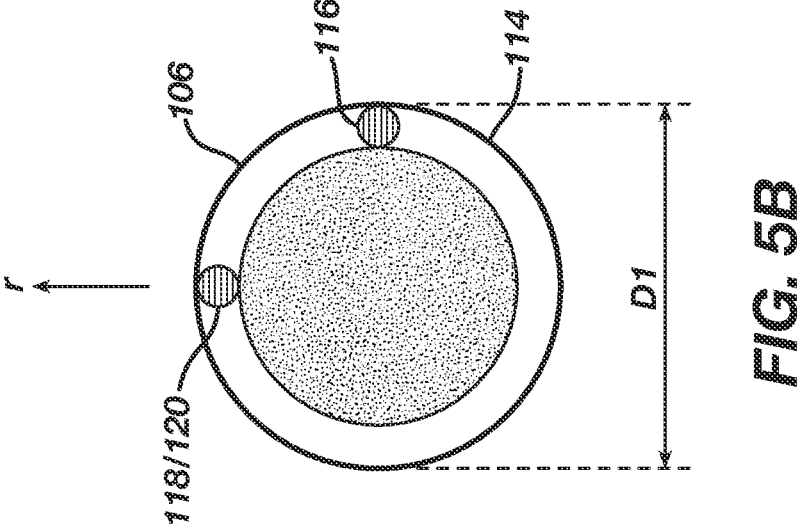
Figure 5A:
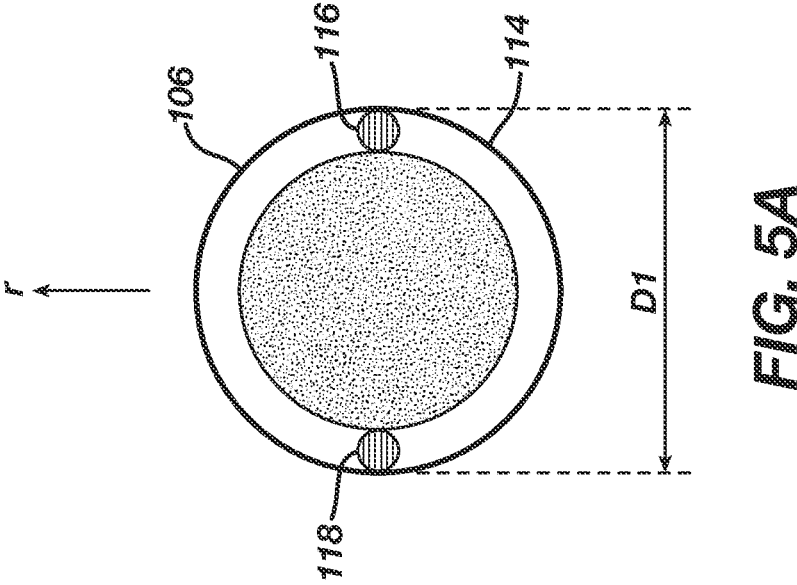

FIGS. 5A and 5B illustrate two example cross-sections of the catheter 100 as indicated in FIGS. 1A & 1B according to aspects of the present disclosure. In particular, FIG. 5A is a cross-sectional view of the distal shaft 106 near the distal end 108 and FIG. 5B is a cross-sectional view of the distal shaft 106 near the transition zone 122. As can be seen, the catheter 100 includes a straight lumen 116, a curved lumen 118, and a shortened lumen 120. The shortened lumen 120 and the curved lumen 118 coexist near the transition zone 122. The curved lumen rotates 90 degrees around the catheter body 103 as it moves from the distal end 108 to the transition zone 122. Thus, when the pull wire 126 in the curved lumen 118 is translated (e.g., pulled from the proximal end 102 or modulated using control handle 101), the distal shaft 106 deflects along the curved path, for example, forming a lasso or loop. The shortened lumen 120 stops between the transition zone 122 and the distal end 108. When the pull wire 126 in the shortened lumen 120 is translated (e.g., pulled from the proximal end 102 or modulated using control handle 101), the catheter 100 deflects about the transition zone 122 along the shortened path, for example, bending the catheter 100 at the transition zone 122. It may be possible to translate the pull wire 126 in the shortened lumen 120 at the same time as translating the pull wires 126 either the straight lumen 116 or the curved lumen 118 in order to change an orientation of the shape of the catheter 100 formed by the straight lumen 116 or the curved lumen 118.

Figure 6B:
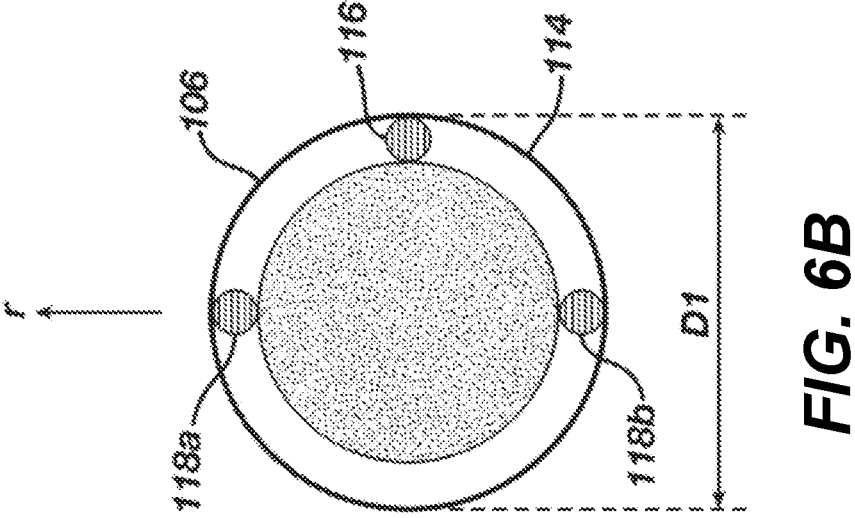
Figure 6A:
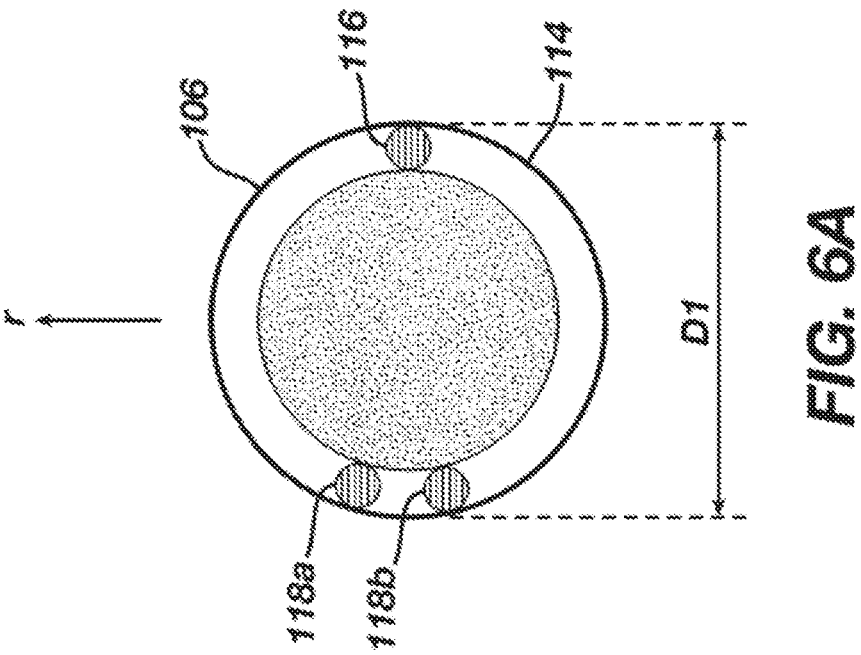

FIGS. 6A and 6B illustrate two example cross-sections of the catheter 100 as indicated in FIGS. 1A & 1B according to aspects of the present disclosure. In particular, FIG. 6A is a cross-sectional view of the distal shaft 106 near the distal end 108 and FIG. 6B is a cross-sectional view of the distal shaft 106 near the transition zone 122. As can be seen, the catheter 100 includes a straight lumen 116 and two curved lumen 118a/118b. The curved lumens 118a and 118b rotate 90 degrees around the catheter body 103 as it moves from the distal end 108 to the transition zone 122 in opposite directions. Thus, when the pull wire 126 in the first curved lumen 118a is translated (e.g., pulled from the proximal end 102 or modulated using control handle 101), the distal shaft 106 deflects along the curved path in one direction, while, when the pull wire 126 in the second curved lumen 118b is translated (e.g., pulled from the proximal end 102 or modulated using control handle 101), the distal shaft 106 deflects along the curved path in the other direction.

Figure 7B:
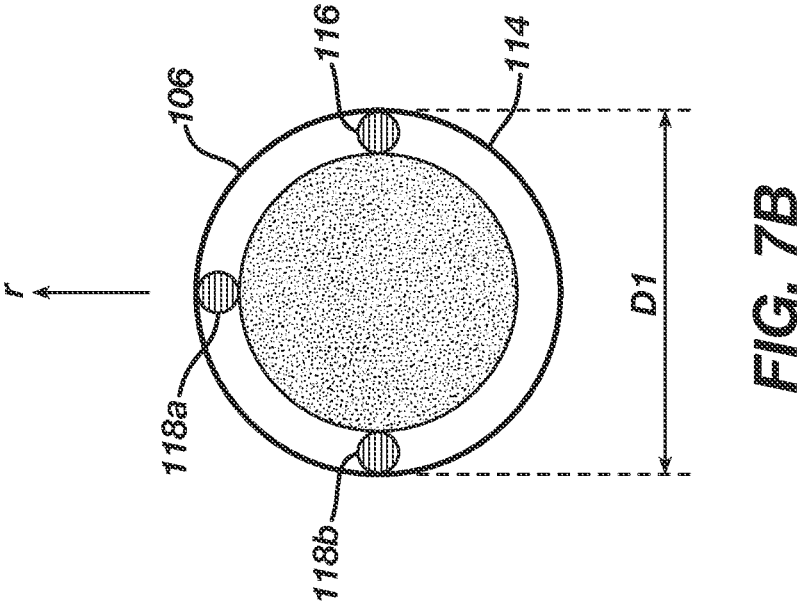
Figure 7A:
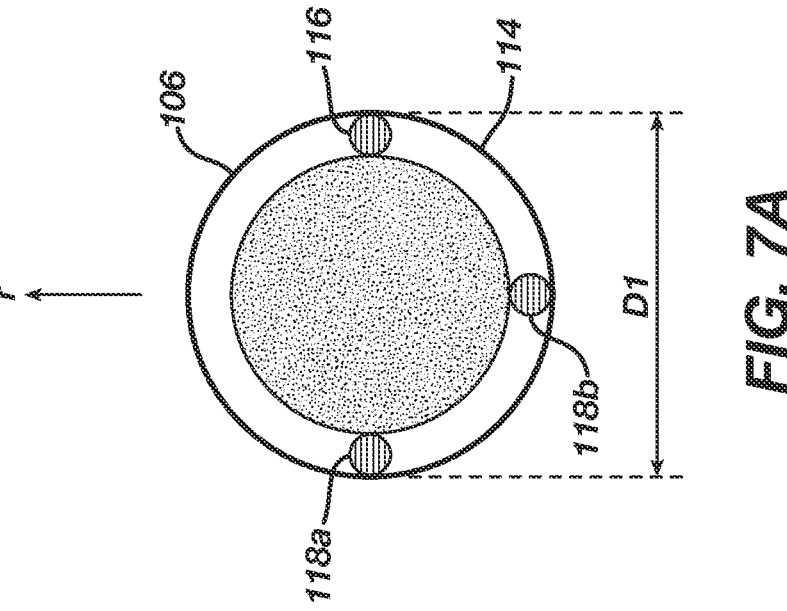

FIGS. 7A and 7B illustrate two example cross-sections of the catheter 100 as indicated in FIGS. 1A & 1B according to aspects of the present disclosure. In particular, FIG. 7A is a cross-sectional view of the distal shaft 106 near the distal end 108 and FIG. 7B is a cross-sectional view of the distal shaft 106 near the transition zone 122. As can be seen, the catheter 100 includes a straight lumen 116 and two curved lumen 118a/118b. The curved lumens 118a and 118b rotate 90 degrees around the catheter body 103 as it moves from the distal end 108 to the transition zone 122, offset by 90 degrees from each other. Thus, when the pull wire 126 in the first curved lumen 118a is translated (e.g., pulled from the proximal end 102 or modulated using control handle 101), the distal shaft 106 deflects along the curved path at one position, while, when the pull wire 126 in the second curved lumen 118b is translated (e.g., pulled from the proximal end 102 or modulated using control handle 101), the distal shaft 106 deflects along the curved path at the other position.

Figure 8B:
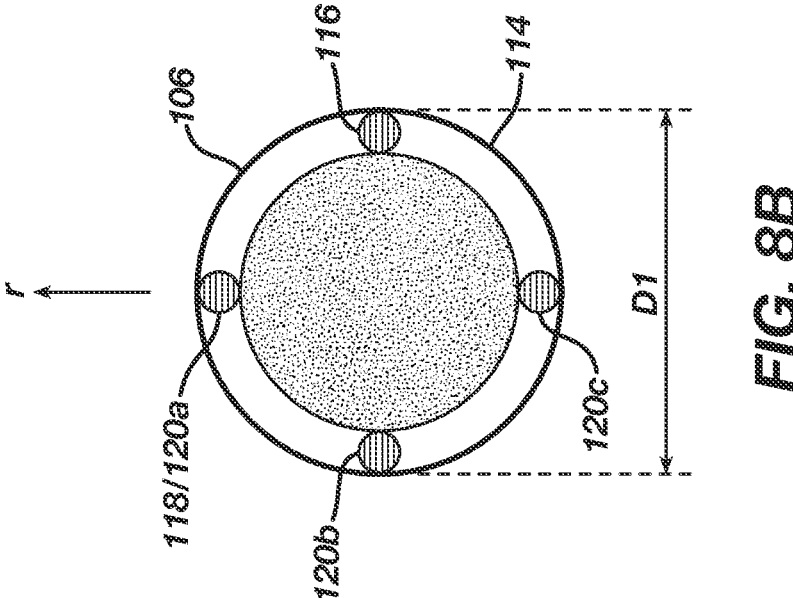
Figure 8A:
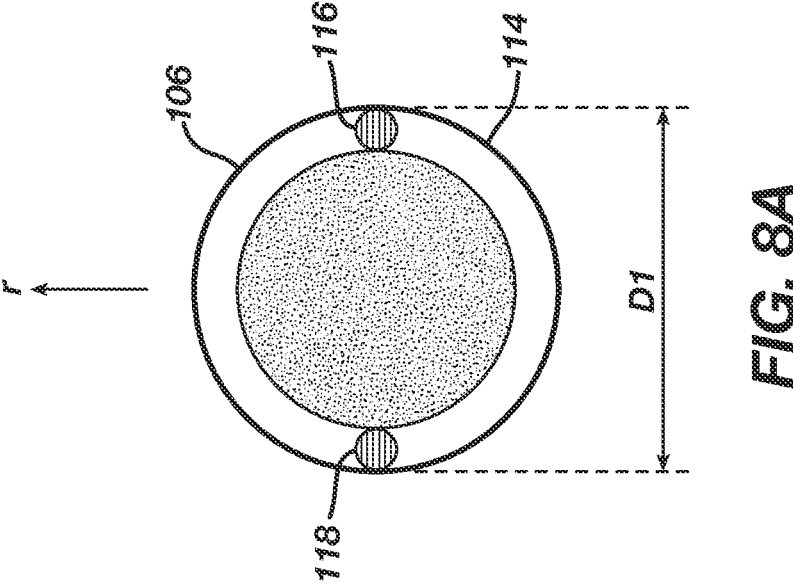

FIGS. 8A and 8B illustrate two example cross-sections of the catheter 100 as indicated in FIGS. 1A & 1B according to aspects of the present disclosure. In particular, FIG. 8A is a cross-sectional view of the distal shaft 106 near the distal end 108 and FIG. 8B is a cross-sectional view of the distal shaft 106 near the transition zone 122. As can be seen, the catheter 100 includes a straight lumen 116, a curved lumen 118, and three shortened lumen 120a, 120b, and 120c. The first shortened lumen 120a and the curved lumen 118 coexist near the transition zone 122. The curved lumen rotates 90 degrees around the catheter body 103 as it moves from the distal end 108 to the transition zone 122. Thus, when the pull wire 126 in the curved lumen 118 is translated (e.g., pulled from the proximal end 102 or modulated using control handle 101), the distal shaft 106 deflects along the curved path, for example, forming a lasso or loop. The shortened lumen 120a, 120b and 120c stop between the transition zone 122 and the distal end 108. When the pull wire 126 in one of the shortened lumen 120a/120b/120c is translated (e.g., pulled from the proximal end 102 or modulated using control handle 101), the catheter 100 deflects about the transition zone 122 along the respective shortened path, for example, bending the catheter 100 at the transition zone 122. It may be possible to translate the pull wire 126 in one of the shortened lumen 120a/120b/120c at the same time as translating the pull wires 126 either the straight lumen 116 or the curved lumen 118 in order to change an orientation of the shape of the catheter 100 formed by the straight lumen 116 or the curved lumen 118.

Figure 9B:
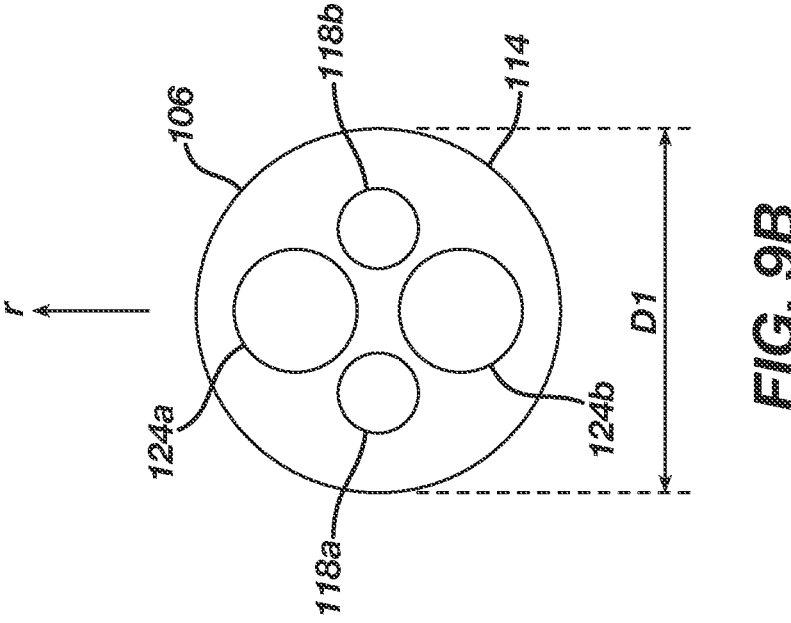
Figure 9A:
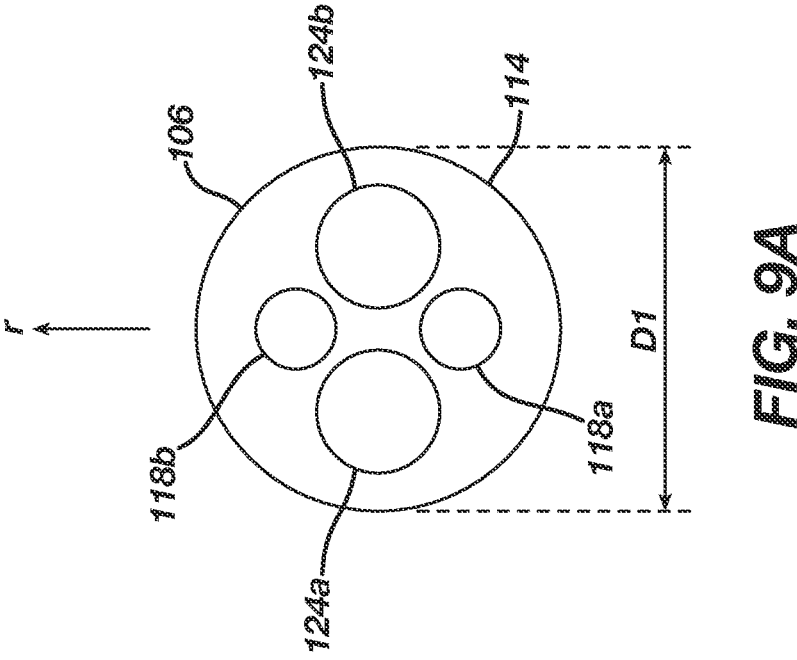

FIGS. 9A and 9B illustrate two example cross-sections of the catheter as indicated in FIGS. 1A & 1B according to aspects of the present disclosure. In particular, FIG. 9A is a cross-sectional view of the distal shaft 106 near the distal end 108 and FIG. 9B is a cross-sectional view of the distal shaft 106 near the transition zone 122. As can be seen, the catheter 100 includes two curved lumen 118a and 118b and two function lumens 124a and 124b. The function lumens 124a and 124b allow for sensors, power, and/or tools to pass through the catheter 100. The curved lumens 118a and 118b rotate 90 degrees around the catheter body 103 as it moves from the distal end 108 to the transition zone 122, offset by 90 degrees from each other. Thus, when the pull wire 126 in the first curved lumen 118a is translated (e.g., pulled from the proximal end 102 or modulated using control handle 101), the distal shaft 106 deflects along the curved path at one position, while, when the pull wire 126 in the second curved lumen 118b is translated (e.g., pulled from the proximal end 102 or modulated using control handle 101), the distal shaft 106 deflects along the curved path at the other position.

Figure 10B:
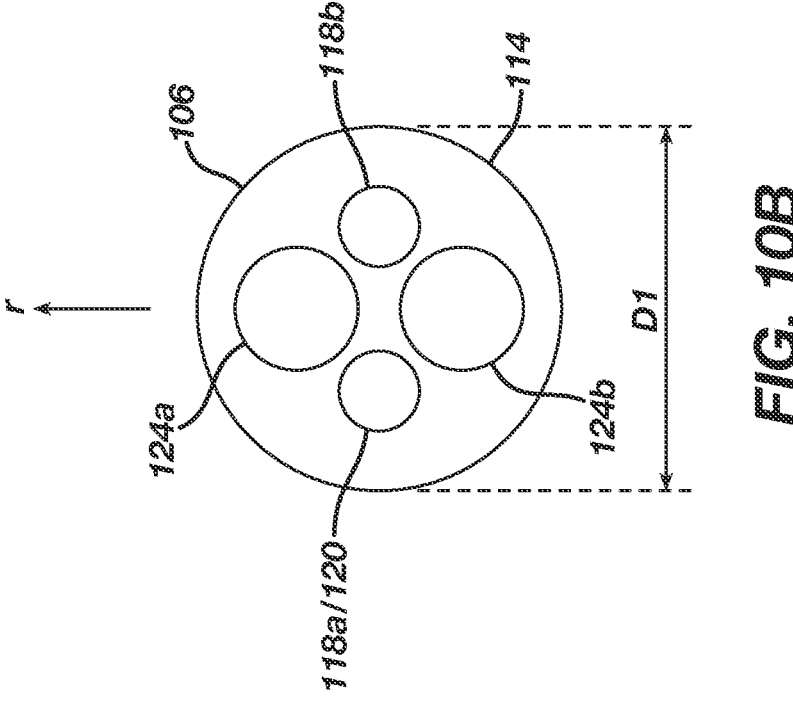
Figure 10A:
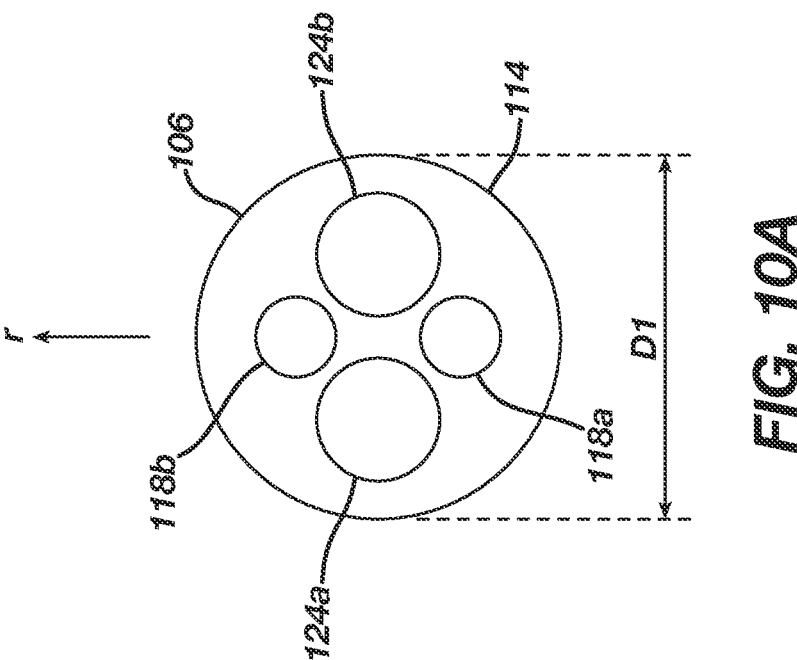

FIGS. 10A and 10B illustrate two example cross-sections of the catheter as indicated in FIGS. 1A & 1B according to aspects of the present disclosure. In particular, FIG. 9A is a cross-sectional view of the distal shaft 106 near the distal end 108 and FIG. 9B is a cross-sectional view of the distal shaft 106 near the transition zone 122. As can be seen, the catheter 100 includes two curved lumen 118a and 118b and two function lumens 124a and 124b. The function lumens 124a and 124b allow for sensors, power, and/or tools to pass through the catheter 100. The first curved lumen 118a attaches to a straight, shortened lumen 120 at the transition zone 122. Thus, the first curved lumen 118a may only be curved about the distal shaft 106 (e.g., where the catheter 100 deflects) and substantially straight about the proximal shaft 104. The curved lumens 118a and 118b rotate 90 degrees around the catheter body 103 as it moves from the distal end 108 to the transition zone 122, offset by 90 degrees from each other. Thus, when the pull wire 126 in the first curved lumen 118a is translated (e.g., pulled from the proximal end 102 or modulated using control handle 101), the distal shaft 106 deflects along the curved path at one position, while, when the pull wire 126 in the second curved lumen 118b is translated (e.g., pulled from the proximal end 102 or modulated using control handle 101), the distal shaft 106 deflects along the curved path at the other position. When the pull wire 126 in the shortened lumen 120 is translated (e.g., pulled from the proximal end 102 or modulated using control handle 101), the catheter 100 deflects about the transition zone 122 along the shortened path, for example, bending the catheter 100 at the transition zone 122. It may be possible to translate the pull wire 126 in the shortened lumen 120 at the same time as translating either pull wires 126 in the curved lumens 118a and 118b in order to change an orientation of the shape of the catheter 100 formed by the curved lumens 118a and 118b.

Although a catheter tube 114 is generally described with reference to FIGS. 2A-10B, one of ordinary skill will recognize in light of the present disclosure that the lumen orientations of catheter tube 114 could be applied a sheath tube 114 without departing from the scope of the present disclosure.

Figure 12:
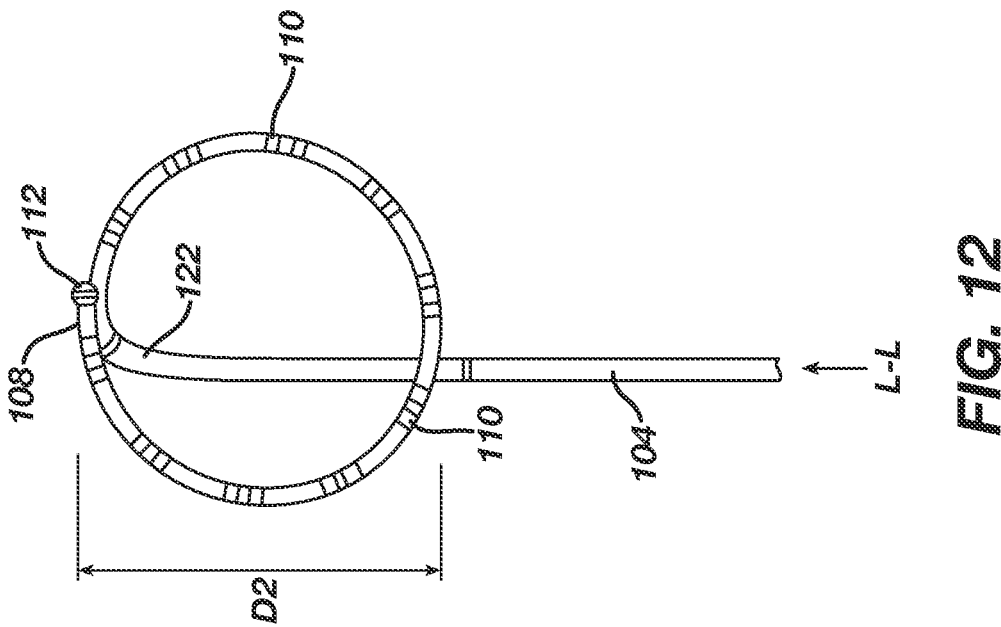
FIGS. 11 and 12 illustrate activation of a pull-wire in a curved lumen of example catheters according to aspects of the present disclosure.
Figure 11:
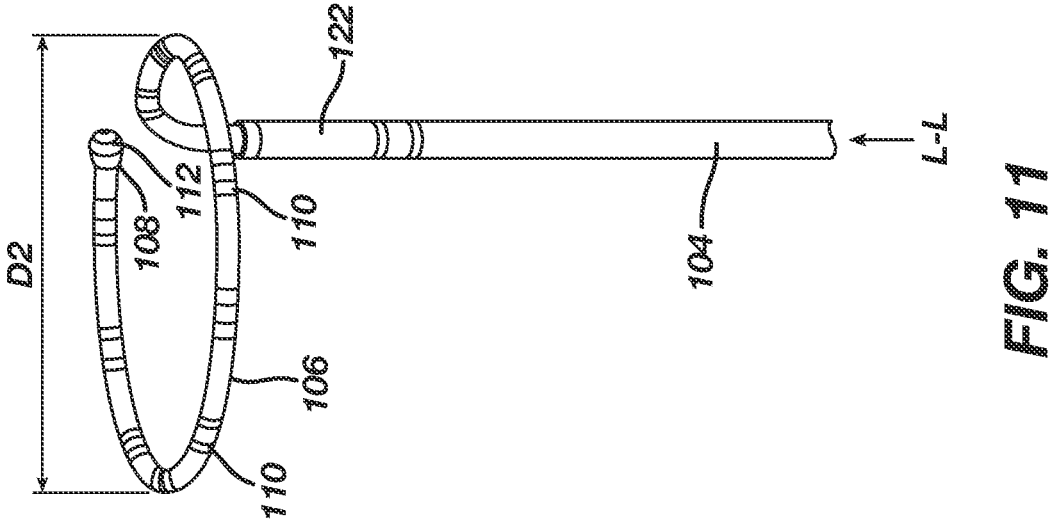

FIGS. 11 and 12 illustrate activation of a pull-wire 126 in a curved lumen 118 of example catheters 100 according to aspects of the present disclosure. As can be seen, when the pull-wire 126 is activated in the curved lumen 118, the distal shaft 106 of the catheter forms a loop of diameter D2. Additionally, when the pull-wire 126 is activated in the shortened lumen 120 the loop is repositioned as the catheter 100 deflects across the transition region 122.

Figure 13A:
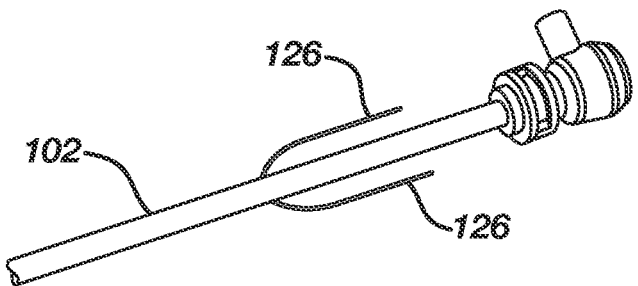
FIGS. 13A and 13B illustrate proximal shafts of example catheters according to aspects of the present disclosure.
Figure 13B:
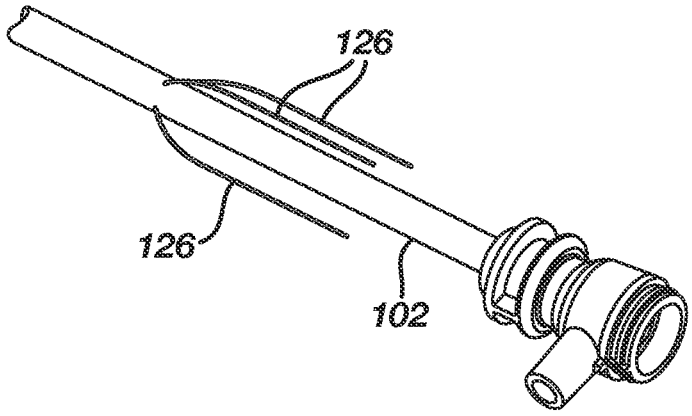

FIGS. 13A and 13B illustrate proximal shafts 105 of example catheters 100 according to aspects of the present disclosure. In FIG. 13A, two pull-wires 126 extend from the proximal shaft 104 of the catheter 100. A first pull-wire could be disposed in a curved lumen 118 and a second pull-wire could be disposed in a straight lumen 116, but this is merely an example. The pull-wires could be activated, for example, by pulling the ends of the pull-wires to deflect the distal shaft 106 of the catheter. FIG. 13B illustrates three pull-wires 126 extending from the proximal shaft 104 of the catheter 100. A first pull-wire could be disposed in a curved lumen 118, a second pull-wire could be disposed in a straight lumen 116, and a third pull-wire can be disposed in a shortened lumen 120, but these are merely examples. The pull-wires could be activated, for example, by pulling the ends of the pull-wires to deflect the distal shaft 106 and/or transition zone 122 of the catheter 100.

Figure 14:
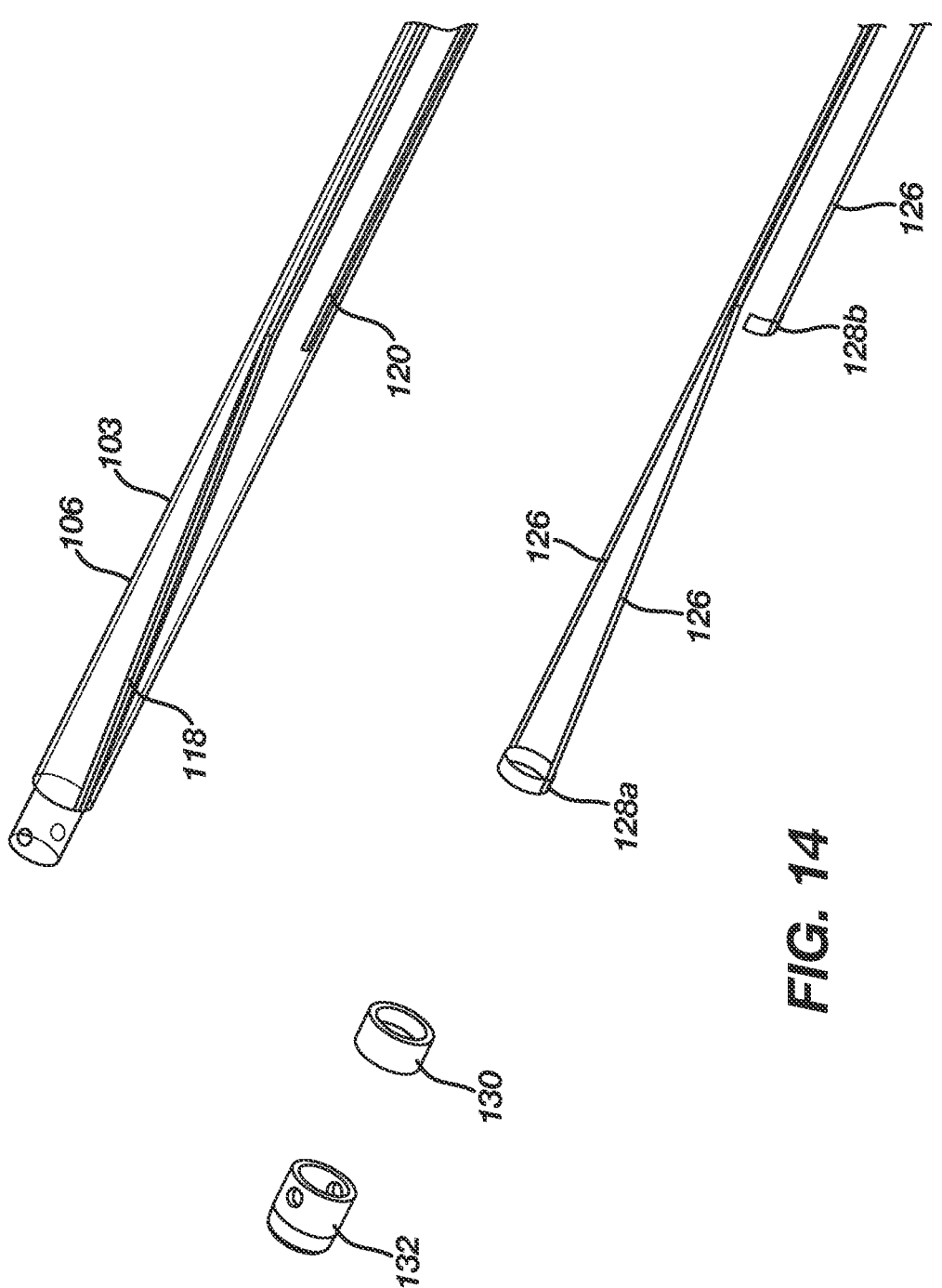
FIG. 14 is an exploded view of an example catheter according to aspects of the present disclosure.

FIG. 14 is an exploded view of an example distal shaft 106 of a catheter 100 according to aspects of the present disclosure. The catheter 100 includes catheter sheath 103 with a curved lumen 118, a shortened lumen 120, and a hidden straight lumen 116. Curved and straight pull-wires 126 for inclusion within the curved and straight lumens 118/116 are attached to a distal pull-wire assembly 128a. A shortened pull-wire 126 is connected to a shortened pull-wire assembly 128b. A support anchor 130 can assist in securing the distal pull-wire assembly 128a to the distal end 108. An atraumatic tip 132 can be included on top of the sheath 103.

Figures 15A, 15B:
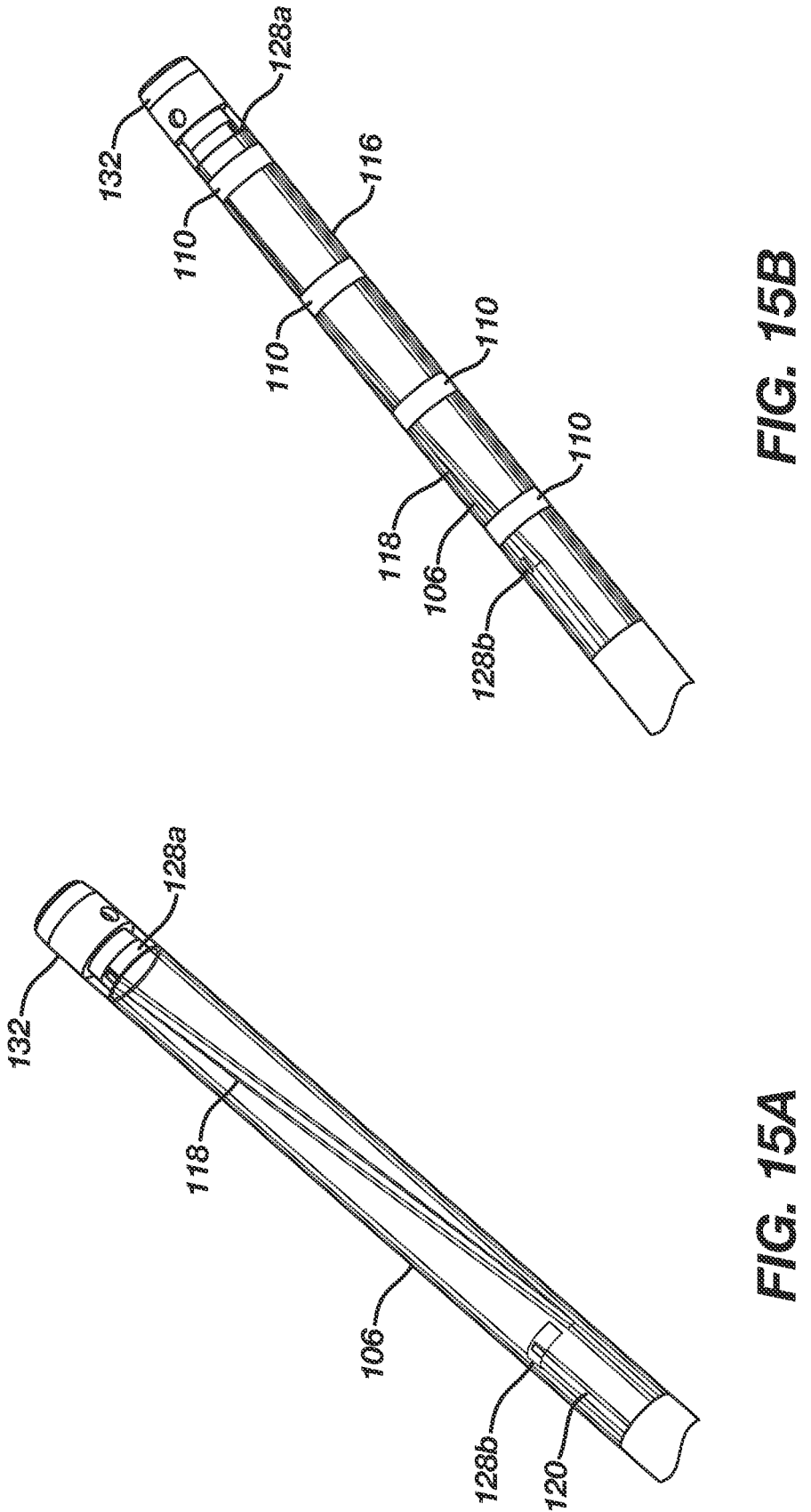
FIGS. 15A and 15B illustrate distal shafts of example catheters according to aspects of the present disclosure.

FIGS. 15A and 15B illustrate distal shafts 106 of example catheters 100 according to aspects of the present disclosure. FIGS. 15A and 15B may illustrate the combined components from FIG. 14. For example, FIGS. 15A and 15B illustrate curved 118 and shortened 120 lumens, distal pull-wire assembly 128a, shortened pull-wire assembly 128b, and atraumatic tip 132. Additionally, FIG. 15B illustrates a plurality of electrodes 110 disposed on a surface of the catheter 100.

Figure 16:
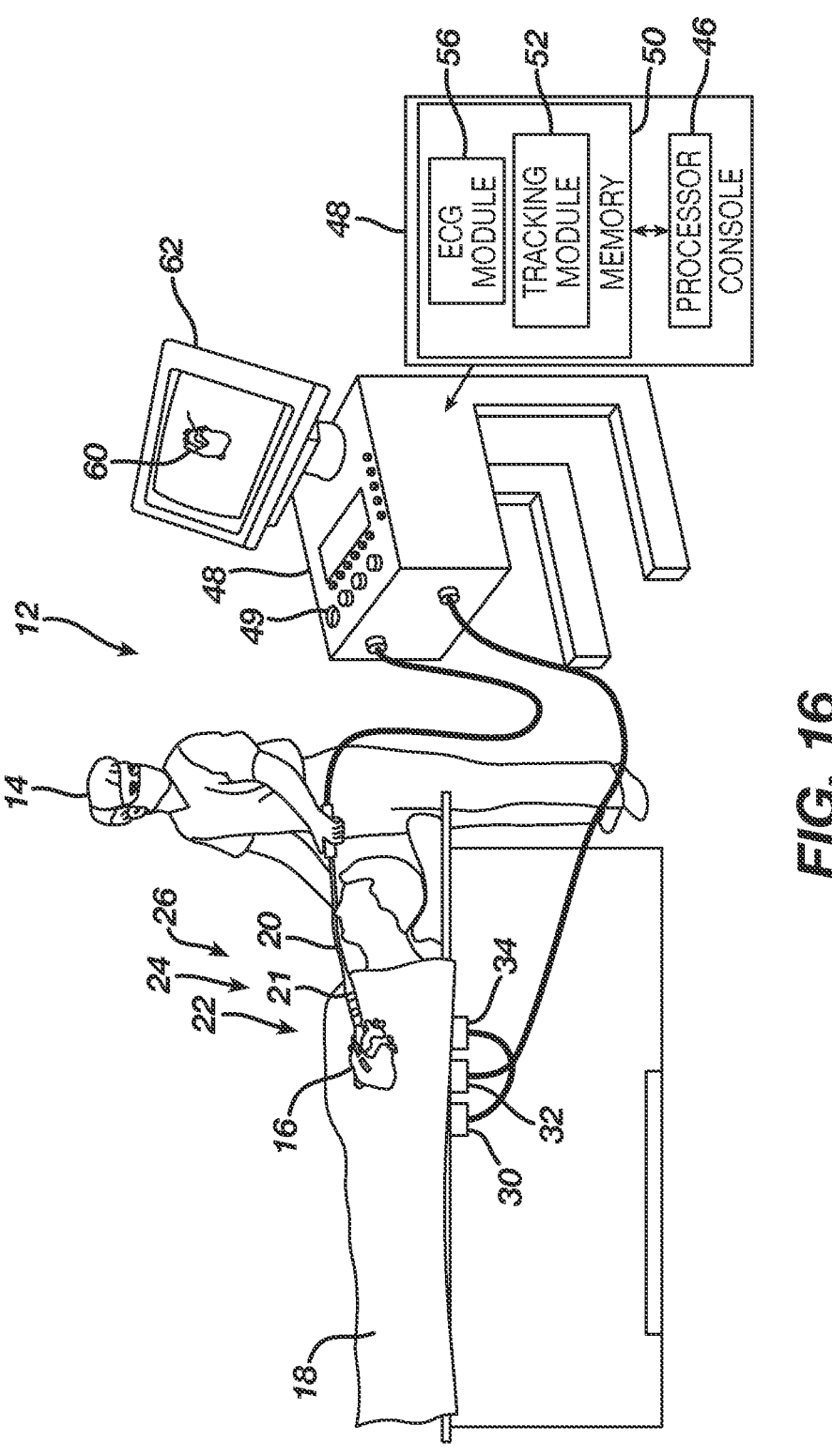
FIG. 16 is an illustration of a treatment incorporating an example catheter according to aspects of the present disclosure.

FIG. 16 is an illustration of a medical treatment with an example system 12 incorporating an example catheter 100 which can be configured similarly to the example catheters 100 illustrated herein, disclosed herein, or a variation thereof as understood by a person skilled in the pertinent art according to the teachings herein. The treatment is performed by a medical professional 14, and, by way of example, the procedure in the description hereinbelow is assumed to comprise an investigation of electropotentials a portion of a myocardium 16 of the heart of a human patient 18. However, example catheters 100 are can be used in other medical treatment procedures as understood by a person skilled in the pertinent art.

In order to perform the investigation, the professional 14 inserts the catheter 100 into a sheath 21 that has been pre-positioned in a lumen of the patient. The sheath 21 is positioned so that the distal shaft 106 of the catheter 100 enters the heart of the patient 18. The distal shaft 106 include a position sensor 24 including three inductive sensors 110 as illustrated herein, disclosed herein, or a variation thereof as understood by a person skilled in the pertinent art according to the teachings herein. The position sensor 24 can enable tracking location and orientation of the distal shaft 106 of the catheter 100. The distal shaft 106 can also include mapping electrodes 188 as illustrated herein, disclosed herein, or a variation thereof as understood by a person skilled in the pertinent art according to the teachings herein. The mapping electrodes 188 can be used to acquire electropotentials of the myocardium 16.

The position sensor 24 includes inductive sensors 110 which respectively include a plurality of coils. While the description herein describes using the coils for sensing magnetic fields, the coils may also be used to produce magnetic fields.

The system 12 can include a console 48 having a system processor 46. The console 48 can include controls 49 which can be usable by the professional 14 to communicate with the processor 46. The software for the processor 46 can be downloaded to the processor in electronic form, over a network, for example. Alternatively, or additionally, the software can be provided on non-transitory tangible media, such as optical, magnetic, or electronic storage media. Tracking (e.g. position and orientation) of distal shaft 106 of the catheter 100 can be displayed on a three-dimensional representation 60 of the heart of patient 18 that is displayed on a screen 62.

In order to operate the system 12, the processor 46 communicates with a memory 50, which has a number of modules used by the processor 46 to operate the system 12. Thus, the memory 50 can include an electrocardiograph (ECG) module 56 which acquires and analyzes signals from the mapping electrodes 188. The memory 50 can also include a tracking module 52, which receives signals from the position sensor 24, and which analyzes the signals in order to generate the location and orientation of distal shaft 106. An ECG module 56 and the tracking module 52 can include hardware and/or software components. The memory 50 can include other software modules, such as a force module for measuring the force on the distal shaft 106, and/or an irrigation module allowing the processor 46 to control irrigation provided for the distal shaft 106. For simplicity, such other modules are not illustrated in FIG. 15.

In addition to receiving and analyzing signals from the position sensor 24, the tracking module 52 can also control radiators 30 32, 34. The radiators can be positioned in proximity to myocardium 16 and can be configured to radiate alternating magnetic fields into a region in proximity to the myocardium 16. The position sensor 24 can be configured to produce electrical signals which can be transmitted to the console 48 to be interpreted by the tracking module 52 to determine a three-dimensional position and orientation of the distal shaft 106 of the catheter 100. Each of the inductive sensors 110 can be configured to generate the electrical signals of the position sensor 24 in response to the radiated magnetic fields traversing coils of the inductive sensors 110, thereby enabling the console 48 to track the distal shaft 106. The Carto® system produced by Biosense Webster uses such a magnetic tracking system.

When the distal shaft 106 is in a correct position, one or more pull-wires 126 can be activated (e.g., pulled) at the proximal end 102 to deflect the distal shaft 106 and or/transition region 122. for example, in a curl or sweep profile, lasso or loop, and/or bend deflection.

The descriptions contained herein are examples of embodiments of the invention and are not intended in any way to limit the scope of the invention. As described herein, the invention contemplates many variations and modifications of the catheter 100 and methods for manufacturing and using the same. Additional modifications that are apparent to those having skill in the art to which this invention pertains and are intended to be within the scope of the claims which follow.

What is claimed is:

1. A catheter comprising:
an elongated body sized to traverse vasculature and comprising:
an outer surface, a proximal end and a distal end disposed on opposite sides thereof with a transition zone disposed therebetween,
a first shaft extending distally from the proximal end of the elongated body to the transition zone and defining a longitudinal axis,
a second shaft extending proximally from the distal end to the transition zone, the second shaft extending axially relative to the longitudinal axis in a delivery configuration, the second shaft bending relative to the longitudinal axis in a deployed configuration;
a first lumen formed in the elongated body and defining:
a first curved lumen path curved about the longitudinal axis and extending fully from the distal end to the transition zone, the first curved lumen path being curved in the delivery configuration, and a first straight lumen path substantially parallel to the longitudinal axis and extending from the transition zone to the proximal end; and
a first pull-wire extending within the first curved and straight lumen paths, the first pull-wire being anchored to the second shaft such that translation of the first pull-wire near the proximal end deflects the second shaft substantially along the first curved lumen path.

2. The catheter of claim 1, a proximal end of the first curved lumen path being connected to the transition zone offset approximately 90 degrees about the longitudinal axis from a distal end of the first curved lumen path connected to the distal end of the elongated body.

3. The catheter of claim 1, a proximal end of the first curved lumen path being connected to the transition zone offset approximately 180 degrees about the longitudinal axis from a distal end of the first curved lumen path connected to the distal end of the elongated body.

4. The catheter of claim 1, the elongated body comprising a substantially circular cross section comprising a diameter, a length of the second shaft being at least about two times the diameter.

5. The catheter of claim 1 further comprising:
a second lumen formed in the elongated body, the second lumen defining a second straight lumen path substantially parallel to the longitudinal axis and extending from the distal end to the proximal end; and
a second pull-wire extending within the second lumen and anchored to the distal end such that translation of the second pull-wire near the proximal end deflects the second shaft substantially along the second straight lumen path.

6. The catheter of claim 1 further comprising:
a second lumen formed in the elongated body, the second lumen defining a second straight lumen path substantially parallel to the longitudinal axis and extending from the proximal end to the transition zone; and
a second pull-wire extending within the second lumen and anchored to the transition zone such that translation of the second pull-wire near the proximal end deflects the transition zone substantially along the second straight lumen path.

7. The catheter of claim 6, an anchor point of the second pull-wire being located proximally along the elongated body relative to a proximal end of the first curved lumen path.

8. The catheter of claim 7, wherein simultaneous translation of the first pull-wire and the second pull-wire near the proximal end deflects the second shaft substantially along the first curved lumen path and deflects the transition zone substantially along the second straight lumen path.

9. The catheter of claim 1 further comprising:
a second lumen formed in the elongated body and defining:
a second curved lumen path curved about the longitudinal axis and extending from the distal end to the transition zone, and
a second straight lumen path substantially parallel to the longitudinal axis and extending from the proximal end to the transition zone; and
a second pull-wire extending within the second lumen and anchored to the second shaft such that translation of the second pull-wire near the proximal end deflects the second shaft substantially along the second curved lumen path.

10. The catheter of claim 9, the first curved lumen path having a clockwise rotational direction about the longitudinal axis as referenced from the distal end and the second curved lumen path has a counterclockwise rotational direction about the longitudinal axis as referenced from the distal end.

11. The catheter of claim 10, the distal end of the first curved lumen path being offset from the distal end of the second curved lumen path.

12. The catheter of claim 1, further comprising a control handle at the proximal end of the elongated body, a proximal end of the first pull-wire being attached to the control handle such that manipulating the control handle tightens the first pull-wire.

13. The catheter of claim 1 further comprising a tip electrode disposed on the second shaft approximate to a distal tip of the second shaft.

14. The catheter of claim 1 further comprising one or more sensing electrodes disposed on the second shaft.

15. The catheter of claim 1 further comprising:
a second lumen formed in the elongated body, the second lumen defining a second lumen path;
a second pull-wire extending within the second lumen and anchored to the elongated body such that translation of the second pull-wire near the proximal end deflects the elongated body substantially along the second lumen path;
a third lumen formed in the elongated body, the third lumen defining a third lumen path; and
a third pull-wire extending within the third lumen and anchored to the elongated body such that translation of the third pull-wire near the proximal end deflects the elongated body substantially along the third lumen path.

16. The catheter of claim 15, wherein
the second lumen path comprises:
a second curved lumen path curved about the longitudinal axis and extending from the distal end to the transition zone, and
a second straight lumen path substantially parallel to the longitudinal axis and extending from the proximal end to the transition zone; and
translation of the second pull-wire near the proximal end deflects the second shaft substantially along the second curved lumen path.

17. The catheter of claim 15, wherein
the third lumen path is substantially parallel to the longitudinal axis and extends from the distal end to the proximal end; and the third pull-wire is anchored to the distal end such that translation of the third pull-wire near the proximal end deflects the second shaft substantially along the third lumen path.

18. The catheter of claim 15, wherein
the third lumen path is substantially parallel to the longitudinal axis and extends from the transition zone to the proximal end; and
the third pull-wire is anchored to the transition zone such that translation of the third pull-wire near the proximal end deflects the transition zone substantially along the third lumen path.

19. The catheter of claim 1, wherein translation of the first pull-wire near the proximal end deflects the second shaft substantially along the first curved lumen path forming a generally circular shape, and further comprising:
a second lumen formed in the elongated body, the second lumen defining a second straight lumen path substantially parallel to the longitudinal axis and extending from the proximal end to the transition zone; and
a second pull-wire extending within the second lumen and anchored to the transition zone such that translation of the second pull-wire near the proximal end deflects the transition zone substantially along the second straight lumen path.

20. A navigable sheath comprising:
an elongated body having a distal end, a proximal end, and a transition zone therebetween, the elongated body being sized to traverse vasculature and comprising:
a first shaft extending distally from the proximal end of the elongated body and defining a longitudinal axis, and
a second shaft extending proximally from the distal end of the elongated body, the second shaft being deflectable, the second shaft extending axially relative to the longitudinal axis in a delivery configuration, the second shaft bending relative to the longitudinal axis in a deployed configuration;
a first lumen formed in the elongated body and comprising a first curved lumen path curved about the longitudinal axis and extending fully proximally from the distal end to the transition zone, the first curved lumen path being curved in the delivery configuration; and
a first pull-wire extending through the first lumen and anchored to the second shaft such that translating the first pull-wire near the proximal end deflects the second shaft substantially along the first curved lumen path.

* * * * *